(12) United States Patent
Daniels et al.

(10) Patent No.: US 12,329,965 B2
(45) Date of Patent: *Jun. 17, 2025

(54) PACING GUIDEWIRE

(71) Applicants: Teleflex Life Sciences LLC, Wilmington, DE (US); Cardiac Interventions and Aviation LLC, Petaluma, CA (US)

(72) Inventors: David Daniels, Petaluma, CA (US); Chad Kugler, Buffalo, MN (US); John Bridgeman, Minneapolis, MN (US); Derek Stratton, Minneapolis, MN (US); Dean Peterson, Minneapolis, MN (US); Joshua Brenizer, Oak Grove, MN (US)

(73) Assignee: Teleflex Life Sciences LLC, Wilmington, DE (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/811,892

(22) Filed: Jul. 12, 2022

(65) Prior Publication Data

US 2022/0339432 A1    Oct. 27, 2022

Related U.S. Application Data

(63) Continuation of application No. 16/936,738, filed on Jul. 23, 2020, now Pat. No. 11,420,046, which is a
(Continued)

(51) Int. Cl.
*A61N 1/375* (2006.01)
*A61M 25/09* (2006.01)
(Continued)

(52) U.S. Cl.
CPC .............. *A61N 1/056* (2013.01); *A61M 25/09* (2013.01); *A61N 1/36507* (2013.01);
(Continued)

(58) Field of Classification Search
CPC ...... A61B 5/287; A61B 5/6851; A61M 25/09; A61N 1/056; A61N 1/36507; A61N 1/36564; A61N 1/375; A61N 1/3752
See application file for complete search history.

(56) References Cited

U.S. PATENT DOCUMENTS 3,769,984 A    11/1973    Muench
4,497,326 A    2/1985     Curry
(Continued)

FOREIGN PATENT DOCUMENTS

CN    102711902 A      10/2012
DE    202010011542 U1  10/2010
(Continued)

OTHER PUBLICATIONS

Aliyev, Farid, et al. "Perforations of right heart chambers associated with electrophysiology catheters and temporary transvenous pacing leads." Turk Kardiyol Dern Ars, 2011, 39(1): 16-22.
(Continued)

*Primary Examiner* — George Manuel
(74) *Attorney, Agent, or Firm* — Dorsey & Whitney LLP

(57) ABSTRACT

Guidewires and methods for transmitting electrical stimuli to a heart and for guiding and supporting the delivery of elongate treatment devices within the heart are disclosed. A guidewire can comprise an elongate body, including first and second elongate conductors, and at least first and second electrodes. A distal end portion of the elongate body can include a preformed bias shape, such as a pigtail-shaped region, on which the first and second electrodes can be located. The preformed bias shape can optionally be non-coplanar relative to an intermediate portion of the elongate body. The first and second elongate conductors can be formed of a single structure or two or more electrically connected structures. The conductors can extend from proximal end portions to distal end portions that electrically
(Continued)

connect to the first and second electrodes. A corewire can extend the length of the elongate body, can at least partially form the first conductor, and can be at least partially surrounded by the second conductor.

20 Claims, 12 Drawing Sheets

Related U.S. Application Data continuation of application No. 16/214,800, filed on Dec. 10, 2018, now Pat. No. 10,758,725, which is a continuation of application No. 15/455,265, filed on Mar. 10, 2017, now Pat. No. 10,173,052.

(60) Provisional application No. 62/436,750, filed on Dec. 20, 2016, provisional application No. 62/378,258, filed on Aug. 23, 2016, provisional application No. 62/346,214, filed on Jun. 6, 2016, provisional application No. 62/310,044, filed on Mar. 18, 2016.

(51) Int. Cl.
*A61N 1/05* (2006.01)
*A61N 1/365* (2006.01)
*A61B 5/00* (2006.01)
*A61B 5/287* (2021.01)

(52) U.S. Cl.
CPC ....... *A61N 1/36564* (2013.01); *A61N 1/3752* (2013.01); *A61B 5/287* (2021.01); *A61B 5/6851* (2013.01); *A61N 1/375* (2013.01)

(56) References Cited

U.S. PATENT DOCUMENTS

| | | |
|---|---|---|
| 4,917,102 A | 4/1990 | Miller et al. |
| 4,957,110 A | 9/1990 | Vogel et al. |
| 5,143,089 A | 9/1992 | Alt |
| 5,190,052 A | 3/1993 | Schroeppel |
| 5,228,453 A | 7/1993 | Sepetka |
| 5,354,327 A | 10/1994 | Smits |
| 5,379,779 A | 1/1995 | Rowland et al. |
| 5,609,622 A | 3/1997 | Soukup et al. |
| 5,807,339 A | 9/1998 | Bostrom et al. |
| 5,824,030 A | 10/1998 | Yang et al. |
| 5,902,331 A | 5/1999 | Bonner et al. |
| 6,106,488 A | 8/2000 | Fleming et al. |
| 6,161,029 A | 12/2000 | Spreigl et al. |
| 6,301,507 B1 | 10/2001 | Bakels et al. |
| 6,356,791 B1 | 3/2002 | Westlund et al. |
| 6,978,185 B2 | 12/2005 | Osypka |
| 6,999,821 B2 | 2/2006 | Jenney et al. |
| 7,094,294 B2 | 8/2006 | Shiota |
| 7,225,035 B2 | 5/2007 | Brabec et al. |
| 7,381,205 B2 | 6/2008 | Thommen |
| 7,702,392 B2 | 4/2010 | Echt et al. |
| 7,715,903 B2 | 5/2010 | Hartley et al. |
| 7,785,273 B2 | 8/2010 | Eskuri |
| 7,918,947 B2 | 4/2011 | Kato |
| 8,639,341 B2 | 1/2014 | Sommer et al. |
| 8,945,208 B2 | 2/2015 | Jimenez et al. |
| 9,031,647 B2 | 5/2015 | Maskara et al. |
| 9,295,813 B2 | 3/2016 | Kanazawa et al. |
| 9,387,323 B2 | 7/2016 | Fleischhacker et al. |
| 9,446,219 B2 | 9/2016 | Lupton |
| 10,173,052 B2 | 1/2019 | Daniels et al. |
| 10,758,725 B2 | 9/2020 | Daniels et al. |
| 10,881,851 B2 | 1/2021 | Daniels et al. |
| 11,420,046 B2 | 8/2022 | Daniels et al. |
| 2002/0002329 A1 | 1/2002 | Avitall |
| 2002/0049476 A1 | 4/2002 | Bardy et al. |
| 2002/0049485 A1 | 4/2002 | Smits |
| 2002/0193836 A1 | 12/2002 | Schmidt |
| 2003/0050681 A1 | 3/2003 | Pianca et al. |
| 2003/0109914 A1 | 6/2003 | Westlund et al. |
| 2003/0114777 A1 | 6/2003 | Griffin et al. |
| 2003/0125780 A1 | 7/2003 | Belden |
| 2003/0212446 A1 | 11/2003 | Kaplan et al. |
| 2004/0024425 A1 | 2/2004 | Worley et al. |
| 2004/0064172 A1 | 4/2004 | McVenes et al. |
| 2004/0260374 A1 | 12/2004 | Zhang et al. |
| 2005/0027343 A1 | 2/2005 | Westlund et al. |
| 2005/0033136 A1 | 2/2005 | Govari et al. |
| 2006/0009828 A1 | 1/2006 | Bemurat et al. |
| 2006/0036306 A1 | 2/2006 | Heist et al. |
| 2006/0106445 A1 | 5/2006 | Woollett |
| 2006/0135953 A1 | 6/2006 | Kania et al. |
| 2006/0259063 A1 | 11/2006 | Bates et al. |
| 2007/0060961 A1 | 3/2007 | Echt et al. |
| 2009/0005846 A1 | 1/2009 | Zhu et al. |
| 2009/0270941 A1 | 10/2009 | Mokelke et al. |
| 2009/0318992 A1 | 12/2009 | Eidenschink et al. |
| 2010/0057072 A1 | 3/2010 | Roman et al. |
| 2010/0228330 A1 | 9/2010 | Bornzin |
| 2010/0318172 A1 | 12/2010 | Schaefer |
| 2011/0071608 A1 | 3/2011 | Fleischhacker et al. |
| 2011/0306867 A1 | 12/2011 | Gopinathan et al. |
| 2012/0016342 A1 | 1/2012 | Brecker |
| 2012/0065624 A1 | 3/2012 | Matsukuma et al. |
| 2012/0130220 A1 | 5/2012 | Maskara et al. |
| 2012/0130397 A1* | 5/2012 | Reddy ............... A61N 1/056 606/129 |
| 2013/0178908 A1 | 7/2013 | Huber |
| 2013/0325086 A1 | 12/2013 | Sommer et al. |
| 2014/0066895 A1 | 3/2014 | Kipperman |
| 2014/0172035 A1 | 6/2014 | Shuros et al. |
| 2014/0330366 A1 | 11/2014 | Dehdashtian et al. |
| 2015/0032027 A1 | 1/2015 | Lupton |
| 2015/0051696 A1 | 2/2015 | Hou et al. |
| 2015/0290432 A1 | 10/2015 | Mathews et al. |
| 2016/0029960 A1 | 2/2016 | Toth et al. |
| 2016/0228013 A1 | 8/2016 | Al-Jilaihawi et al. |
| 2017/0266433 A1 | 9/2017 | Daniels et al. |
| 2017/0266434 A1 | 9/2017 | Daniels et al. |
| 2017/0281910 A1 | 10/2017 | Whisenant et al. |
| 2019/0105490 A1 | 4/2019 | Daniels et al. |
| 2020/0030583 A1 | 1/2020 | Martin et al. |
| 2020/0353241 A1 | 11/2020 | Daniels et al. |
| 2023/0390552 A1 | 12/2023 | Daniels et al. |

FOREIGN PATENT DOCUMENTS

| | | |
|---|---|---|
| DE | 102011109880 | 6/2013 |
| EP | 0109178 B1 | 5/1992 |
| EP | 1561489 A2 | 8/2005 |
| EP | 1208867 B1 | 3/2010 |
| EP | 2480282 B1 | 8/2015 |
| JP | 2013505781 A | 2/2013 |
| WO | 1998036794 A1 | 8/1998 |
| WO | 2008011261 A2 | 1/2008 |
| WO | 2008051554 A2 | 5/2008 |
| WO | 2011037978 A2 | 3/2011 |

OTHER PUBLICATIONS

Banaszewski, Marek, et al. "Right heart perforation by pacemaker leads." Arch Med Sci, 2012, 8(1): 11-13.
European Extended Search Report and Opinion mailed Jul. 14, 2021 in EP Application No. 21169704.0.
Guerios, Enio E. et al. "Left Ventricular Guidewire Pacing for Transcatheter Aortic Valve Implantation," Catheterization and Cardiovascular Interventions, 82, pp. E919-E921 (2013).
Holmes Jr., David R., et al. "Iatrogenic Pericardial Effusion and Tamponade in the Percutaneous Intracardiac Intervention Era," JACC Cardiovasc Interv, 2009, 2(8): 705-17.
Navarini, Susanne et al. "Left Ventricular Guidewire Pacing to Simplify Aortic Balloon Valvuloplasty," Catheterization and Cardiovascular Interventions, 73: 426-427 (2009).
PCT 2nd Written Opinion mailed Dec. 7, 2017 in application PCT/US2017/021719 filed Mar. 10, 2017.

(56) References Cited

OTHER PUBLICATIONS

PCT Article 34 amendments filed Jul. 20, 2017 in connection with application No. PCT/US2017/021719 filed Mar. 10, 2017.
PCT International Preliminary Report on Patentability mailed Feb. 2, 2018 in application PCT/US2017/021719 filed Mar. 10, 2017.
PCT International Search Report mailed May 11, 2017 in application PCT/US2017/021719 filed Mar. 10, 2017.
PCT Written Opinion mailed May 11, 2017 in application PCT/US2017/021719 filed Mar. 10, 2017.

* cited by examiner

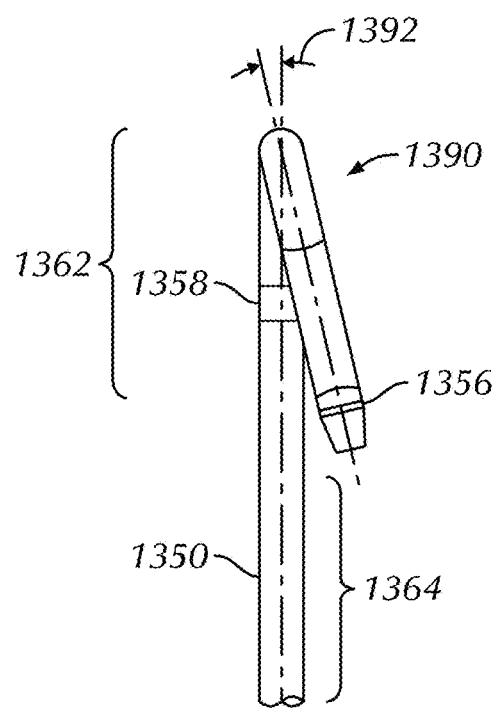
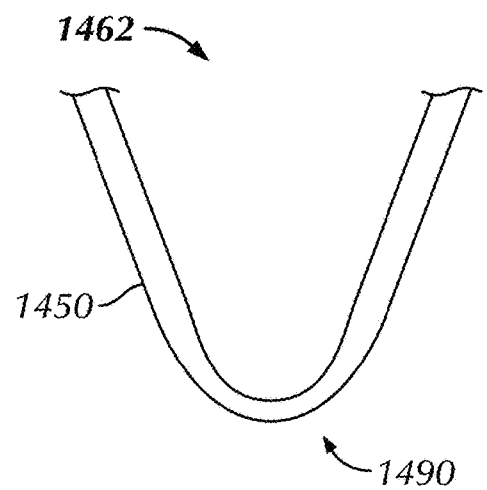
FIG. 13
FIG. 14
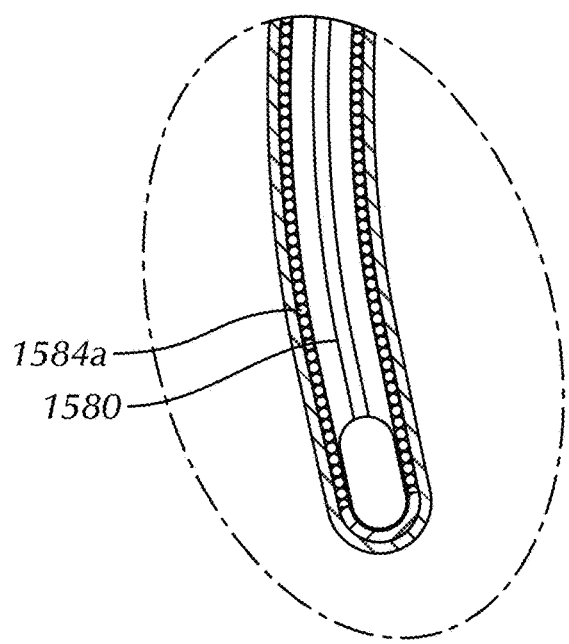
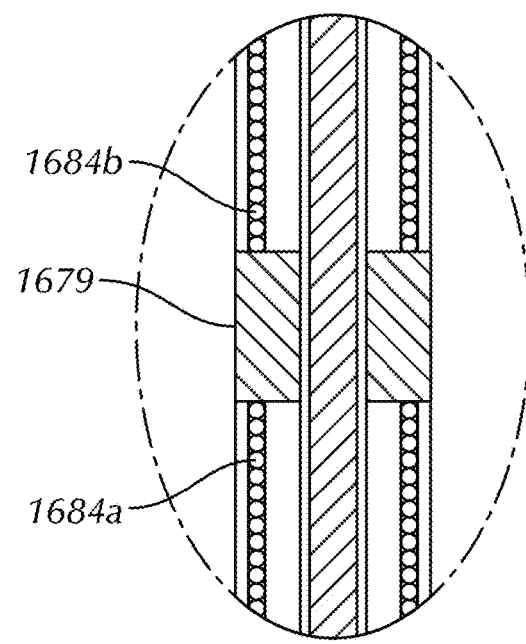
FIG. 15
FIG. 16

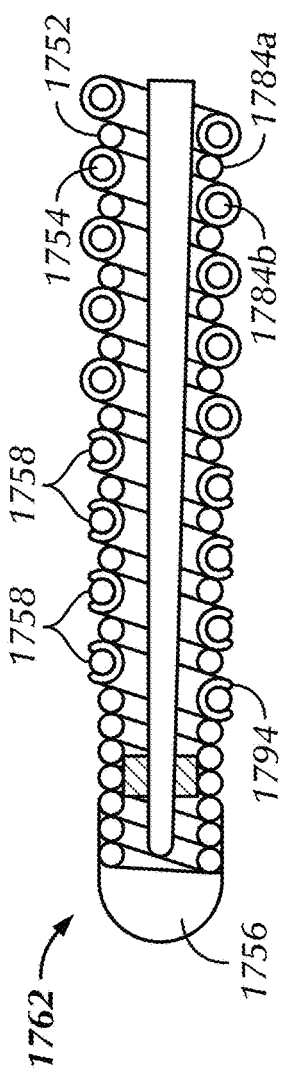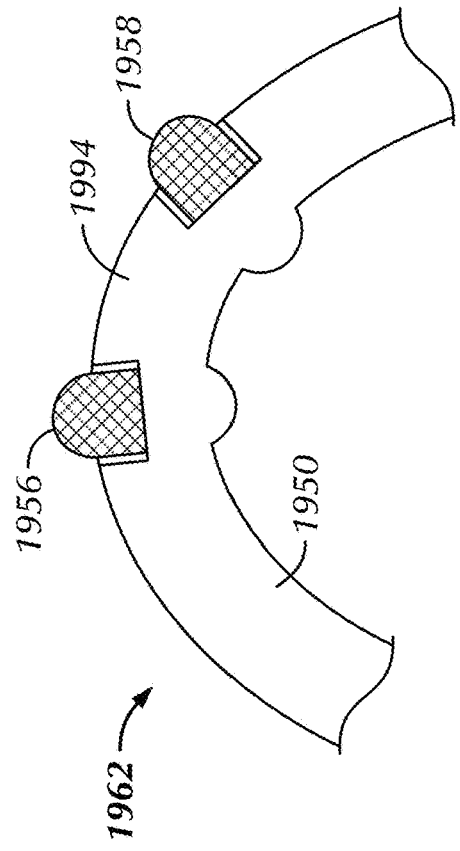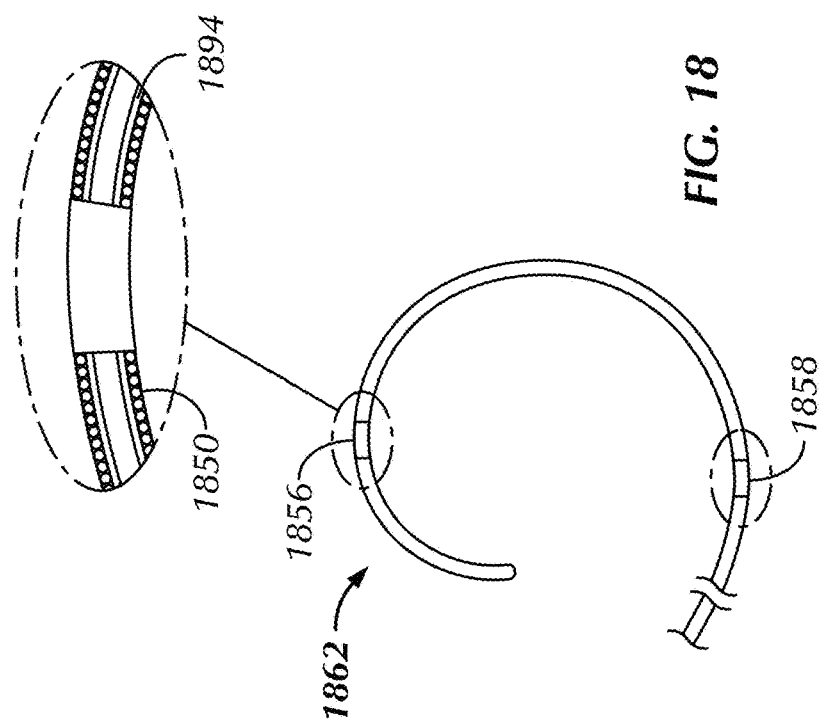

PACING GUIDEWIRE

CLAIM OF PRIORITY

This is a continuation of U.S. patent application Ser. No. 16/936,738, entitled "PACING GUIDEWIRE" and filed Jul. 23, 2020, now U.S. Pat. No. 11,420,046, which is a continuation of U.S. patent application Ser. No. 16/214,800, entitled "PACING GUIDEWIRE" and filed Dec. 10, 2018, now U.S. Pat. No. 10,758,725, which is a continuation of U.S. patent application Ser. No. 15/455,265, entitled "PACING GUIDEWIRE" and filed Mar. 10, 2017, now U.S. Pat. No. 10,173,052, which claims the benefit of priority under 35 U.S.C. § 119 (e) to Daniels et al., U.S. Provisional Patent Application Ser. No. 62/310,044, entitled "PACING GUIDEWIRE" and filed on Mar. 18, 2016, to Daniels et al., U.S. Provisional Patent Application Ser. No. 62/346,214, entitled "PACING GUIDEWIRE" and filed on Jun. 6, 2016, to Daniels et al., U.S. Provisional Patent Application Ser. No. 62/378,258, entitled "PACING GUIDEWIRE" and filed on Aug. 23, 2016, and to Daniels et al., U.S. Provisional Patent Application Ser. No. 62/436,750, entitled "PACING GUIDEWIRE" and filed on Dec. 20, 2016, each of which is herein incorporated by reference in its entirety.

TECHNICAL FIELD

This patent document relates to medical devices. More particularly, but not by way of limitation, the patent document relates to guidewires.

BACKGROUND

Heart valve replacement may be indicated when there is a narrowing of a native heart valve or when the native valve leaks or regurgitates, such as when the valve's leaflets are calcified.

The native valve can be excised and replaced with either a biologic tissue valve or a mechanical valve. Mechanical valves require lifelong anticoagulant medication to prevent blood clot formation, and clicking of the valve can often be heard through a patient's chest. Biologic tissue valves typically do not require such medication and do not click. Tissue valves can be obtained from cadavers or can be porcine or bovine based, and the valves can be attached to cloth-covered synthetic rings or leaflet support frames that are securable to a patient's heart valve annulus.

Conventional heart valve surgery is an open heart procedure conducted under general anesthesia with significant concomitant risks, including bleeding, infection, stroke, heart attack, arrhythmia, renal failure, adverse reactions to the anesthesia medications, or sudden death. An incision is made through the patient's sternum, and the patient's heart is stopped while blood flow is rerouted through a heart-lung bypass machine. The first two or three days following conventional heart valve surgery are often spent in an intensive care unit where heart functions can be closely monitored. The average hospital stay following conventional heart valve surgery is between one and two weeks, with several more weeks required for complete recovery.

Advancements in minimally-invasive surgery and interventional cardiology have encouraged some physicians to pursue percutaneous replacement of a heart valve, including the deployment of an expandable prosthetic heart valve device across the native diseased heart valve (which permanently holds the native valve open). The prosthetic heart valve device can be designed for percutaneous delivery in a cardiac catheterization laboratory under local anesthesia using fluoroscopic guidance, thereby avoiding general anesthesia and open-heart surgery.

OVERVIEW

The present inventors recognize that guidewires play an important role in the field of percutaneous replacement of a heart valve, including percutaneous transcatheter aortic valve implantation (TAVI), transcatheter aortic valve replacement (TAVR), balloon valvuloplasty (BV) or transcatheter mitral valve replacement (TMVR). The present inventors further recognize that there is a need for guidewires and related methods that can reduce the time for, and increase the chances of, a successful percutaneous implantation of a prosthetic heart valve device.

This patent document discloses pacing guidewires that facilitate the performance of TAVI, TAVR, BV or TMVR procedures by (i) providing good support for the over-the-wire (OTW) delivery of elongate treatment devices with low chance of perforation or other damage of vessels, the native aortic or mitral valve, or cardiac tissues through which the guidewire is inserted, and (ii) inducing and maintaining cardiac ventricular tachycardia during certain phases of such procedures. A pacing guidewire can comprise an elongate body, including first and second conductors, and at least first and second electrodes. The elongate body can extend from a proximal end portion to a distal end portion with an intermediate portion therebetween. The at least first and second electrodes have one of a positive or negative polarity and can be spaced between 1 centimeter (cm) and 10 cm apart, for example, in varying configurations along a preformed bias shape at the distal end portion of the elongate body. The first elongate conductor can extend from a proximal end portion to a distal end portion that is electrically connected to the first electrode. Similarly, the second elongate conductor can extend from a proximal end portion to a distal end portion that is electrically connected to the second electrode.

A method for transmitting electrical stimuli to a patient's heart and for guiding and supporting the OTW delivery of elongate treatment devices within the heart can include advancing a distal end portion of a pacing guidewire into a patient's left ventricle such that first and second electrodes are positioned against or near a ventricular wall. Electrical stimuli can be transmitted through the guidewire to the first and second electrodes to induce and maintain cardiac ventricular tachycardia. In various examples, the electrical stimuli transmitted through the guidewire can result in a current flow of 4.0 mA or less, 3.0 mA or less, 2.5 mA or less, or 2.0 mA or less between the electrodes. While the heart is in a state of ventricular tachycardia, a medical procedure, such as dilatation balloon expansion within a native aortic or mitral valve, can be performed.

These and other examples and features of the present pacing guidewires and methods will be set forth, at least in part, in the following Detailed Description. This Overview is intended to provide non-limiting examples of the present teachings—it is not intended to provide an exclusive or exhaustive explanation. The Detailed Description below is included to provide further information about the present guidewires and methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in this patent document.

FIGS. 9-14 are enlarged schematic illustrations of distal end portions of example pacing guidewires.

FIG. 15 is a schematic illustration of an example electrical connection between two structures forming an elongate conductor, such as the electrical connection at portion labeled 15 of the pacing guidewire of FIG. 10.

FIG. 16 is a schematic illustration of an example insulation configuration to electrically isolate first and second elongate conductors, such as the insulation configuration at portion labeled 16 of the pacing guidewire of FIG. 10.

FIGS. 17-19 are enlarged schematic illustrations of example electrode configurations designed to stimulate heart tissue.

Figure 1:
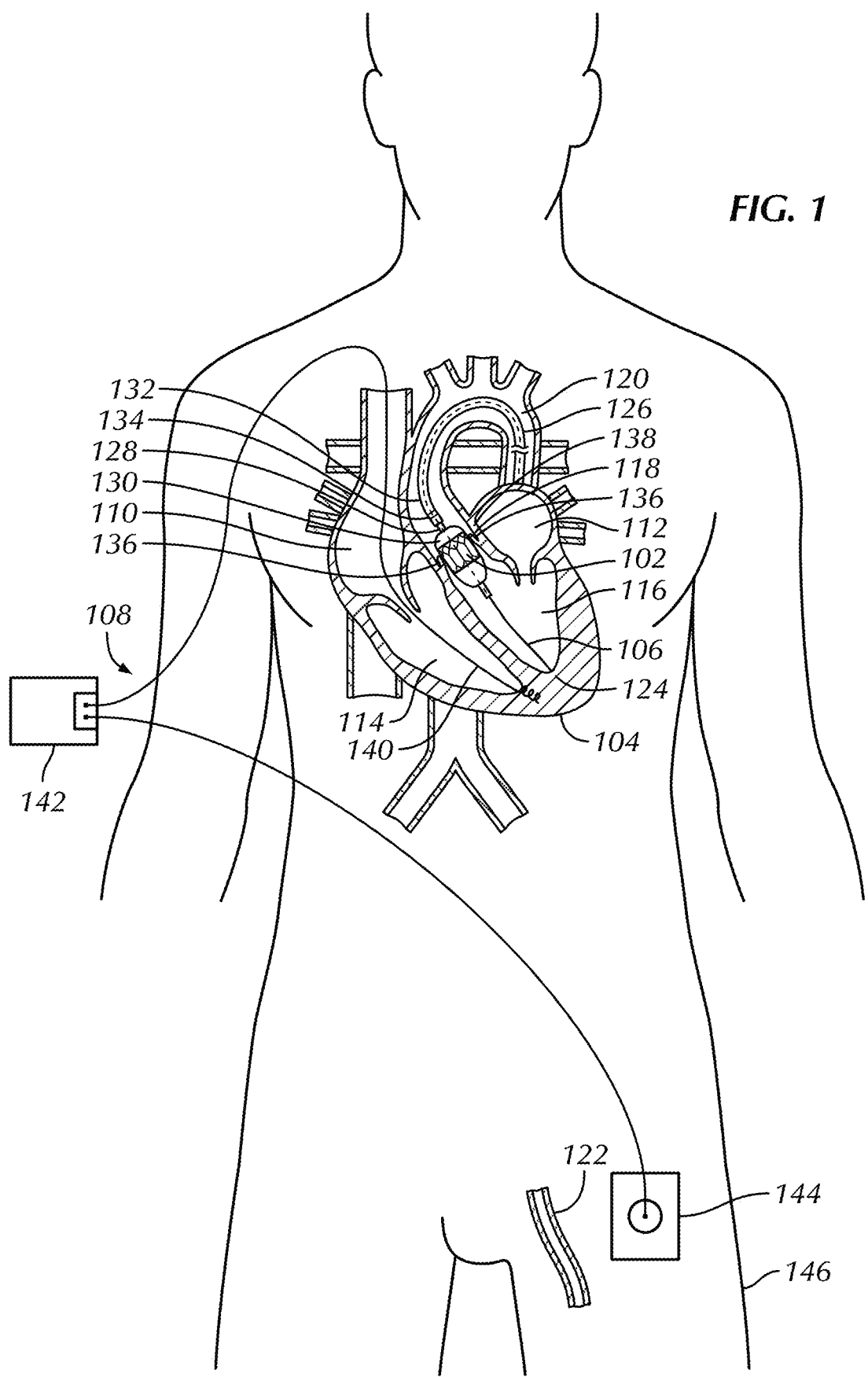
FIG. 1 is a schematic illustration of the implantation of a prosthetic aortic heart valve using a conventional guidewire and a dedicated right ventricular lead pacing means.

The drawing figures are not necessarily to scale. Certain features and components may be shown exaggerated in scale or in schematic form, and some details may not be shown in the interest of clarity and conciseness.

DETAILED DESCRIPTION

Definitions

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document.

The terms "proximal" and "distal" refer to a position or direction relative to a treating physician. "Proximal" and "proximally" refer to a position that is closer to, or in a direction toward, the physician. "Distal" and "distally" refer to a position that is distant, or in a direction away, from the physician and opposite the proximal direction.

The term "patient" refers to mammals and includes both humans and animals.

The singular forms "a", "an", and "the" include plural referents unless the content clearly dictates otherwise. As used in this specification and the appended claims, the term "or" is generally employed in its sense including "and/or" unless the content clearly dictates otherwise.

All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure.

The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.).

Existing Transfemoral TAVI, TAVR, BV and TMVR Procedures:

FIG. 1 is a schematic illustration of a prosthetic aortic heart valve 102 being implanted into a heart 104 using a conventional guidewire 106. The heart 104 includes a right atrium 110, a left atrium 112, a right ventricle 114 and a left ventricle 116. The left ventricle 116 connects to a body's arteries by way of an aortic valve 118 and an ascending aorta 120. As part of the valve implantation procedure, the guidewire 106 can be inserted through a guide catheter that extends from a femoral artery 122, through the ascending aorta 120, and within the aortic valve 118 of the patient. The guidewire 106 can be advanced through the guide catheter until its distal end portion locates, or nests against, the apex 124 of the left ventricle 116. With the guidewire 106 positioned inside the heart 104 and serving as an OTW support structure for the rest of the valve implantation procedure, the guide catheter can be removed from the patient.

An introducer sheath 126 can be inserted over the guidewire 106 and into the ascending aorta 120, and subsequently a balloon catheter 128 having a dilatation balloon 130 on its distal end portion can be passed over the guidewire and through the sheath. A physician can locate a distal tip 132 of the introducer sheath 126 using a radiopaque marker(s) 134 and fluoroscopy, or using other imaging systems such as transesophageal echo, transthoracic echo, intravascular ultrasound imaging (IVUS), or an injectable dye that is radiopaque. The dilatation balloon 130 can be expanded radially outward into contact with native aortic valve leaflets 136 as part of a BV procedure. With information concerning the size of the particular aortic valve 118, the balloon 130 can be chosen so that it expands outward and nominally compresses the aortic valve leaflets 136 against surrounding aortic walls 138.

The physician or operating room staff can then crimp the expandable prosthetic aortic heart valve 102 over the dilatation balloon 130. Currently, there are two primary expandable prosthetic heart valves 102 available in the U.S. to select from—the Edwards-Sapien™ heart valve (Edwards Lifesciences, Irvine, CA) and the CoreValve™ device (Medtronic, Minneapolis, MN). The Edwards-Sapien is a tri-leaflet bovine pericardial valve within a tubular balloon expandable stent. Both retrograde (i.e., transfemoral) and antegrade (i.e., transapical) approaches can be used depending on patient characteristics. The CoreValve is a tri-leaflet porcine pericardial valve with a self-expanding nitinol stent. This valve can be used via a retrograde approach via transfemoral, subclavian, axillary or direct aortic access.

With the prosthetic heart valve 102 crimped over the balloon 130, the physician can once again advance the balloon catheter 128 over the guidewire 106 and through the introducer sheath 126 until the prosthetic heart valve is located at the aortic annulus between the native aortic leaflets 136. When the physician is satisfied with the positioning and rotational orientation of the prosthetic heart valve 102, the balloon 130 can be expanded into gripping contact with the aortic annulus. The term "gripping contact" can imply sufficient contact to ensure that the prosthetic heart valve 102 does not migrate after expansion. Once the valve 102 is properly implanted, the physician can deflate the balloon 130 and withdraw the balloon catheter 128 over the guidewire 106. The introducer sheath 126 can then be withdrawn simultaneously with, or followed by, the guidewire 106.

During existing TAVI, TAVR, BV and TMVR procedures, temporary right ventricular rapid pacing 108, which has been associated with a small but recognized rate of morbidity, is performed in order to induce and maintain a ventricular tachycardia. The ventricular tachycardia can lower the patient's blood pressure to allow balloon deployment in the aortic annulus without balloon embolization from cardiac flow, and it can assure more accurate placement of the prosthetic heart valve 102 being implanted. The traditional way of temporary pacing involves a femoral or jugular venous puncture to place the distal end portion of a unipolar pacing lead 140 in or on a wall of the right ventricle 114. A proximal end portion of the lead 140 can be connected to a first pole of an external pulse generator 142 with an alligator clamp, and a second opposite pole of the external pulse generator 142 can be electrically connected to a large surface skin electrode 144 placed at a left thigh 146 of the patient, for example. The skin electrode 144 can be used as a return electrode for the single lead electrode.

In an effort to streamline TAVR and other valve-related procedures and avoid attendant complications, the present inventors have investigated use of a 0.035 in (0.89 mm) left ventricular delivery wire as a pacing lead. Though this concept is conceptually appealing, in practice the use of guidewires for pacing is challenging since existing wires are not insulated against current loss in blood and therefore: cannot be tested for ventricular capture until they are insulated within a patient's body such as with a valvuloplasty balloon or a TAVR device; cannot provide obligate pacing following TAVR without the valvuloplasty balloon or TAVR device left in place; can only provide unipolar pacing in conjunction with a grounding contact in or on subcutaneous tissue and a non-dedicated connection to an electrical source; and have high pacing capture thresholds and low safety margins due to unipolar pacing.

The guidewires and methods disclosed in this patent document include a purpose built rail device with insulated poles capable of consistent left ventricular pacing at low thresholds with or without a delivery system (e.g., a valvuloplasty balloon or a TAVR device) in place. The pacing guidewires and related methods can improve procedural safety and efficiency by providing the dual purpose of (i) transmitting electrical stimuli to the heart 104 for inducing and maintaining a ventricular tachycardia, and (ii) guiding and supporting the OTW delivery of elongate treatment devices (e.g., a balloon catheter) for successful implantation of the prosthetic aortic heart valve 102. It is believed that pacing the heart 104 using a left ventricular bipolar guidewire can be a beneficial alternative to conventional transvenous temporary right ventricular pacing 108 in the context of TAVI, TAVR, BV and TMVR procedures. Among other things, this pacing alternative obviates the need for an additional venous puncture and avoids the cost, discomfort, and risk of perforating the right ventricle 114 with the temporary unipolar pacing lead 140.

In the description that follows, the present pacing guidewires are shown as having a design that is optimized for use in connection with TAVI, TAVR or BV procedures. For example, a guidewire can be designed with a sufficient degree of flexibility to facilitate negotiation of tortuous anatomy and to minimize trauma to cardiac tissue, while also maintaining a certain level of stiffness, particularly in the aortic valve region, in order to provide adequate support for items delivered thereon (e.g., aortic valve implantation systems) and to sit comfortably within the left ventricle 116 in a stable, atraumatic manner. It should be noted, however, that the present pacing guidewires are not limited to use in TAVI, TAVR and BV procedures. The guidewires could be similarly utilized in a wide variety of percutaneous medical procedures, such as gastrointestinal or hepatobiliary procedures, as well as alternative types of coronary procedures such as TMVR, without departing from the scope of the present patent document.

Figure 2:
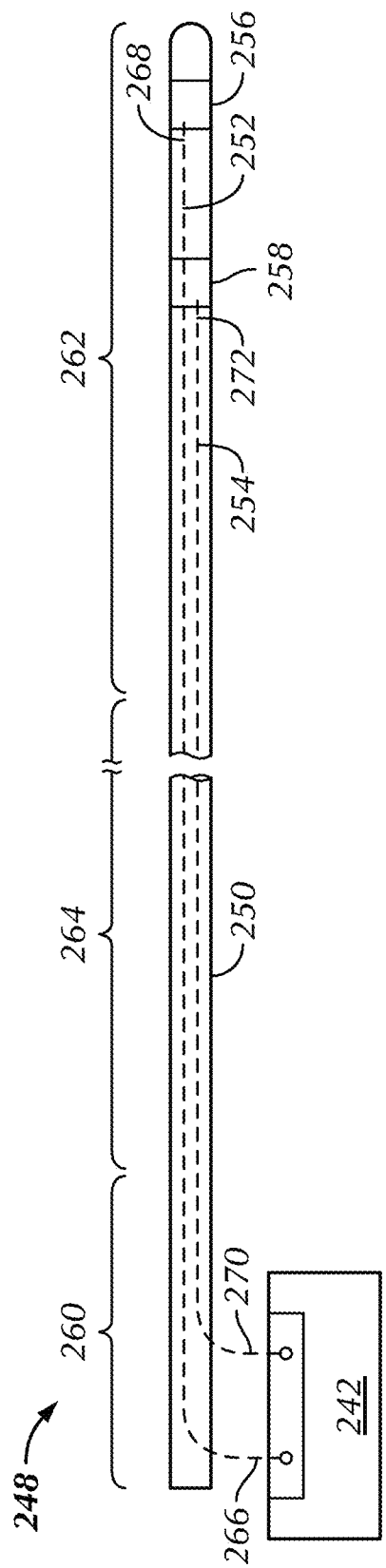
FIG. 2 is a schematic illustration of an example pacing guidewire configured to transmit electrical stimuli from an external pulse generator to the heart and guide and support the OTW delivery of elongate treatment devices.

Pacing Guidewires of Present Subject Matter:

FIG. 2 is a schematic illustration of a pacing guidewire 248 including an elongate body 250 carrying a first elongate conductor 252, a second elongate conductor 254, and at least two electrodes 256, 258 for delivering electrical stimuli to a heart, such as to a left ventricle of the heart. Portions of the elongate body 250 can include a lubricious coating (e.g., a coating including hydrophilic, polytetrafluoroethylene (PTFE), silicone or other dry lubricious material) to ease its advancement through a guide catheter and to facilitate the OTW delivery and withdrawal of devices guided over it. In an example, a first portion of the elongate body 250 has a silicone coating and a second portion of the body has a hydrophilic coating. The coating(s) can be applied by dip coating, spraying, or shrink wrapping a hollow tube of such material over the outer surface of the elongate body 250.

Indicia suitable for viewing by a physician, thereby providing a distinguishing characteristic from non-pacing guidewires and other interventional tools that may be used during a procedure, can be applied to the coating(s) or the elongate conductors 252, 254. The indicia can be applied to the coating(s) before or after their application to the elongate body 250. Alternatively, the indicia can be applied to the conductors 252, 254 and a transparent or light-colored coating can be applied over the conductors for visibility of the darker indicia. The indicia can include one or more continuous helical strips, individual discontinuous circumferential stripes, or other axially spaced apart indicia along the length of the guidewire. The indicia can be bi-color, tri-color, or any combination of colors that are discernable. The indicia can be about 1 mm to 4 mm wide and spaced apart by a similar distance for clarity. The indicia can extend over the entire length of the elongate body 250 or solely over a certain portion(s) of the length.

The elongate body 250 can extend from a proximal end portion 260 to a distal end portion 262, with an intermediate portion 264 therebetween. The proximal end portion 260 can be manipulated by the physician from a position outside of a patient's body. The distal end portion 262 can include a flexible tip to facilitate traversal through the body to one or more target pacing sites. The elongate body 250 can have any suitable length for use in conducting electrical stimuli from an external pulse generator 242 to the heart of the patient, such as from about 100 cm to about 300 cm. The elongate body 250 can have a circular cross-section for facilitated insertion through portions of the body. The diameter of the elongate body 250, including insulation, can be in the range of about 0.014 in (0.36 mm) to about 0.038 in (0.97 mm), such as about 0.035 in (0.89 mm), although other sizes are also possible.

The first and second conductors 252, 254 allow the guidewire 248 to function as a bipolar pacing wire. The first conductor 252 can extend longitudinally from a terminal contact at a proximal end portion 266, through or along the elongate body 250, to a distal end portion 268 electrically connected to at least the first electrode 256. The second conductor 254 can similarly extend longitudinally from a terminal contact at a proximal end portion 270, through or along the elongate body 250, to a distal end portion 272 electrically connected to at least the second electrode 258. Each conductor 252, 254 can be formed of a single structure or multiple structures, which are electrically joined together such as by soldering or welding. The conductors 252, 254 can be highly flexible small diameter metal filaments, stranded cables, helical coils constructed of circular wire or flat wire (allowing for diametrical space savings), corewires, braids, hypotubes or electrically-conductive polymer layers constructed from a conductive, low resistance material, such as MP35N® alloy (SPS Technologies, Jenkintown, PA), Elgiloy® alloy (Elgiloy Specialty Metals, Sycamore, IL), tungsten, platinum, silver, stainless steel, polyacetylene or combinations thereof, for example.

The first and second electrodes 256, 258 can be coaxially or eccentrically mounted along the elongate body 250 and can spaced apart by a predetermined distance, such as a distance between about 1 cm and 10 cm, with insulation in between. In some examples, more than two electrodes—such as three, four or five electrodes—can be mounted along the elongate body 250. The electrodes 256, 258 can be cylindrical in shape and can have an axial length between about 2 mm and about 20 mm, for example, for delivery of electrical stimuli to the heart. At least one electrode can serve as the anode and at least one other electrode can serve as the cathode. The present inventors have found that limiting the collective axial length of cylindrical electrodes of each polarity to 12 mm or less, and particularly 10 mm or less, can provide a beneficial, more concentrated current density to heart tissue. For example, if the second conductor 254 is electrically connected to three cylindrical electrodes, the collective axial length of those three electrodes can be 12 mm or less, or 10 mm or less. Alternatively, one of both of the electrodes 256, 258 can have a non-cylindrical, strip-like (channel-like) shape axially extending for lengths between about 1 cm and 10 cm, for example. Each electrode can be made up of one strip or multiple strips. The strip(s) can be straight and extend along one side of the guidewire or can have a spiral configuration that wraps around the guidewire.

In operation, AC stimuli signals created by the external pulse generator 242 can be applied to the electrodes 256, 258. The pulse generator 242 can include means for delivering time-spaced pulses to the electrodes 256, 258 for suitable pacing. Current on the order of about 4.0 mA or less, 3.0 mA or less, 2.5 mA or less, or 2.0 mA or less, for example, can flow through blood or other fluid between the spaced apart electrodes 256, 258.

Figure 3:
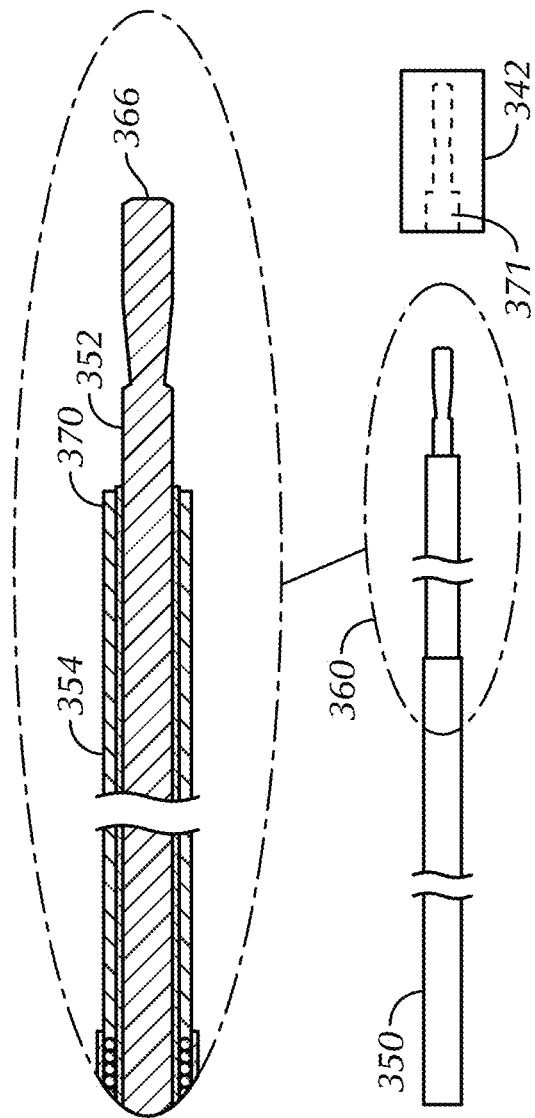
FIG. 3 is an enlarged schematic illustration of a proximal end portion of an example pacing guidewire.

FIG. 3 is an enlarged schematic illustration of a proximal end portion 360 of an example pacing guidewire's elongate body 350. In this example, a first conductor 352 can be at least partially in the form of a corewire, and a second conductor 354 can be at least partially in the form of a braid or hypotube. Each conductor 352, 354 can include a dedicated terminal contact brought out from the elongate body 350 at its proximal end portion 366, 370. The terminal contacts can be in-line with one another for direct electrical connection with an external pulse generator 342 via a generator receptacle 371, or indirect electrical connection with the pulse generator 342 via a dedicated connector body. Any other suitable method of effecting electrical connection between the conductors 352, 354 and the pulse generator 342 can also be employed.

Figure 4:
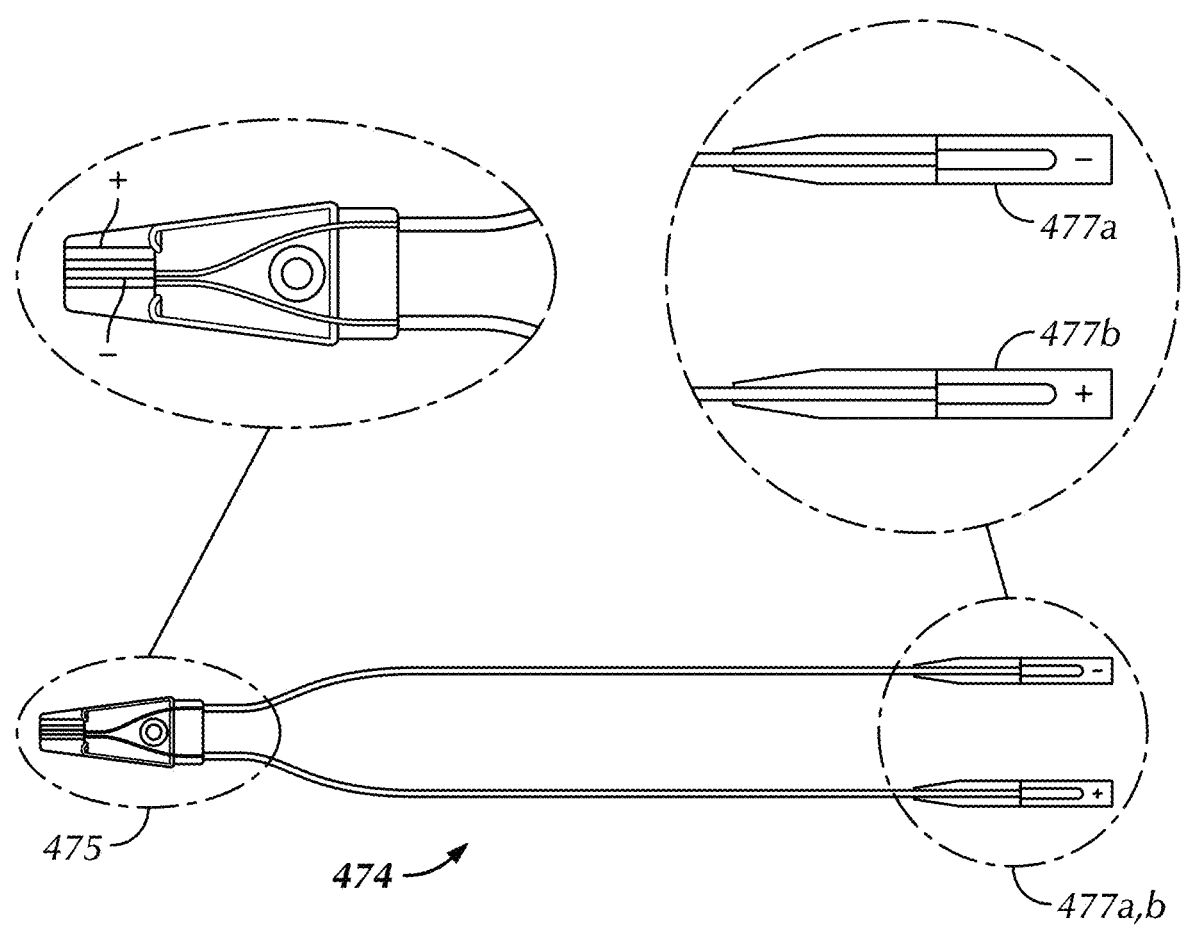
FIG. 4 is a schematic illustration of an example connector body, which is removably couplable to a proximal end portion of a pacing guidewire.

FIG. 4 is a schematic illustration of an example connector body 474 removably couplable to a proximal end portion of a pacing guidewire's elongate body. The connector body 474 can include a guidewire connection portion 475 and pulse generator connection portions 477a, 477b. The guidewire connection portion 475 can be slid on and off the proximal end portion of the pacing guidewire's elongate body and can include an entrance seal member to electrically isolate conductors of the pacing guidewire from bodily and medical fluids present in the treatment area. The pulse generator connection portions 477a, 477b can provide an electrical extension of the guidewire's conductors and can be color-coded or otherwise marked for identification of each conductor's polarity. In this example, pulse generator connection portion 477a has a negative polarity (cathode) and pulse generator connection portion 477b has a positive polarity (anode). The pulse generator connection portions 477a, 477b can make electrical connections with the pulse generator by way of alligator clips, for example.

FIGS. 5-8 are enlarged schematic illustrations, in section, of intermediate portions 564, 664, 764, 864 of an example pacing guidewire's elongate body 550, 650, 750, 850. The elongate body 550, 650, 750, 850 can include one or more tapers and constant diameter regions, which can be manifested in variations in the size of the outer diameter, the inner diameter and the wall thickness of body components. Any tapers and constant diameter regions can be formed by any one of a number of different techniques, for example, by centerless grinding methods, stamping methods, extrusion methods, co-extrusion methods, and the like.

Figure 5:
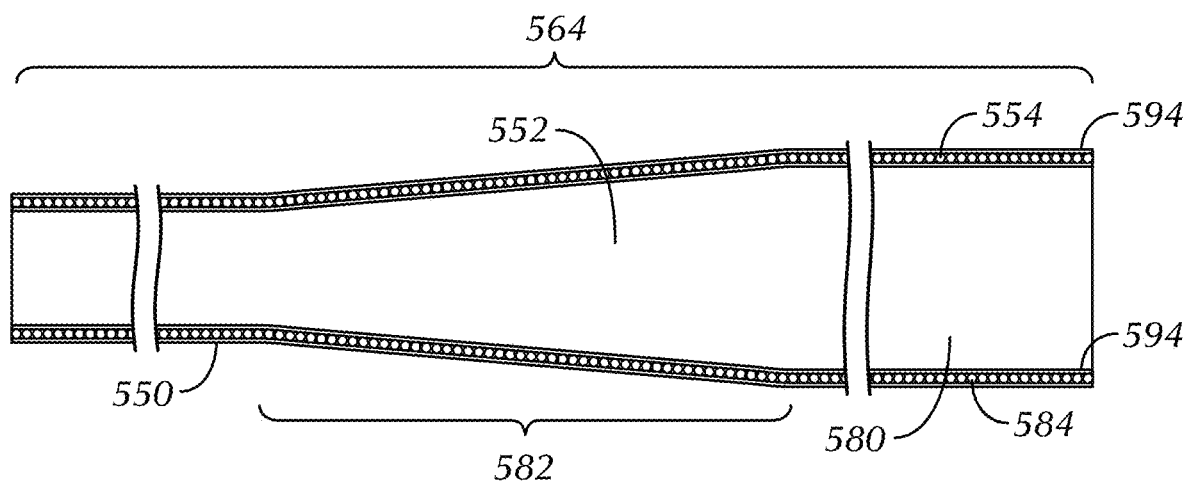
FIGS. 5-8 are enlarged schematic illustrations, in longitudinal cross-section, of intermediate portions of example pacing guidewires.
Figure 6:
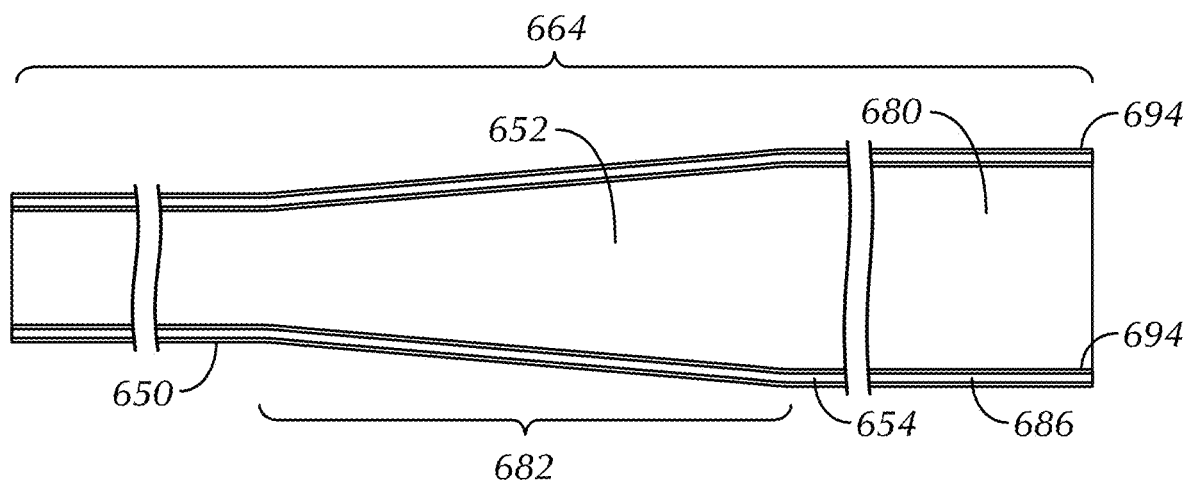
Figure 8:
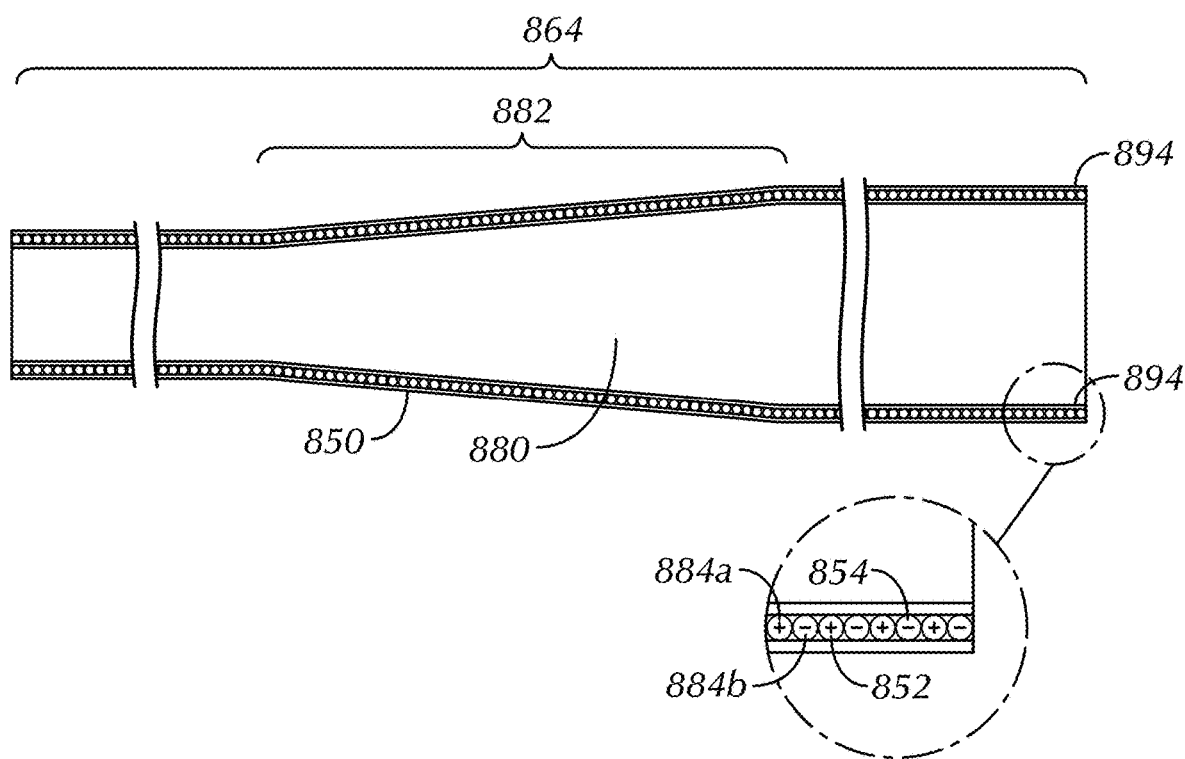

A corewire 580, 680, 780, 880 can extend from a proximal end portion to a distal end portion of the elongate body 550, 650, 750, 850. The corewire can have a gradual reduction (or taper) 582, 682, 882 in its cross-sectional diameter through the intermediate portion 564, 664, 864, as shown in the examples of FIGS. 5, 6 and 8. This gradual reduction 582, 682, 882 can provide the elongate body 550, 650, 850 with a diminishing degree of stiffness and increased flexibility towards its distal end portion. By enhancing its flexibility, the distal end portion of the elongate body 550, 650, 850, which can be designated for placement against sensitive myocardial tissues and structures, is less likely to impart potentially harmful forces. At the same time, the intermediate portion 564, 664, 764, 864 can maintain an adequate degree of stiffness to support the OTW delivery of critical components, such as a dilatation balloon or a prosthetic aortic valve.

The transition in cross-sectional diameter along the corewire 580, 680, 880 can be provided in a subtle manner to render the guidewire more resistant to kinking upon the application of stress. The present inventors have found that regions in a corewire with rapid transitions in cross-sectional diameter are more susceptible to the formation of sharpened bends or kinks during use. The creation of sharpened bends or kinks in the corewire can be problematic in that they can introduce traumatic forces against a point on a ventricular wall, for example, thereby perforating or otherwise damaging heart tissue, and can catch on a device slidably mounted over the guidewire.

Figure 7:
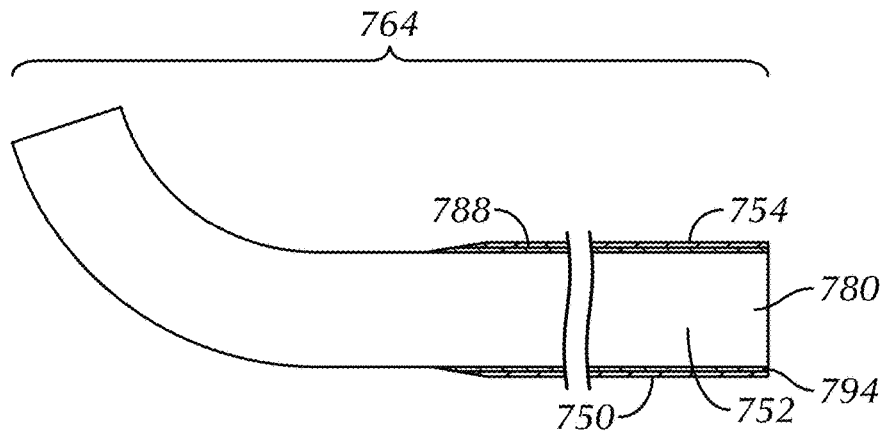

As shown in the examples of FIGS. 5-7, the corewire 580, 680, 780 can be made from an electrically-conductive material and, as such, can at least partially form one of the guidewire's conductors 552, 652, 752, while the second of the guidewire's conductors 554, 654, 754 can surround a portion of the corewire and can take the form of a helical coil 584 (FIG. 5), an electrically-conductive polymer layer 686 (FIG. 6), a hypotube 788 (FIG. 7), a braid or a combination thereof.

In the example of FIG. 5, the helical coil 584 can be secured to the corewire 580 at each of its ends using a bonding agent, such as an electrically-insulating, non-conductive epoxy, but otherwise free-floating relative to the corewire 580. The helical coil 584 can be a single filar coil or a multi-filar coil.

In the example of FIG. 6, the electrically-conductive polymer 686 can be of tubular form or alternatively in the form of a tape that is helically wrapped about the corewire 680. Conductive polymers fall into two general categories: intrinsically conductive and conductor-filled. Intrinsically conductive polymers can include polyacetylene, polypyrrole and polyaniline, among others. Alternatively, conductor-filled polymers can include presently available materials approved for implantation such as silicone rubber with embedded metallic, carbon or graphite particles or powder.

In the example of FIG. 7, the corewire 780 can be concentric and slide inside the hypotube 788. This design can enable a proximal electrode to be placed at a desired location, and a distal electrode can be extended a variable distance beyond the proximal electrode.

As shown in the example of FIG. 8, the corewire 880 can be electrically neutral and at least partially surrounded by first and second conductors 852, 854 in the form of helical coils 884a, 884b. Two conductive wires can be in coaxially wound into a single helical form. The wires can be insulated from one another prior to winding and can optionally be of differing diameters, as shown in the example of FIG. 17. Alternatively, a first conductor can be wound into a helical coil of a diameter less than a winding of a second conductor.

The helical coil(s) 584, 884a, 884b, electrically-conductive polymer layer 686, or hypotube 788 can extend a substantial length of the corewire 580, 680, 780, 880 or can extend solely around its proximal end, intermediate 564, 664, 764, 864, and/or distal end portions. The present inventors have found that helical coils extending the entire length of the corewire require electricity to travel a relatively long distance and can increase the electrical resistance associated with an electrical path between an external pulse generator and distally-positioned electrodes. Accordingly, a low resistance linear filament, stranded cable, hypotube, or braid can be used to travel a portion of the length of the corewire and bridge the electrical path between the external pulse generator and an intermediate- or distally-positioned helical coil portion acting as an electrode, for example.

An insulative sheath or other member 594, 694, 794, 894 comprising non-conductive material can be disposed about the outer surface of the corewire 580, 680, 780, 880, helical coil(s) 584, 884a, 884b, electrically-conductive polymer layer 686, hypotube 788, or braid to electrically insulate the components from one another and from surrounding body tissue when implanted. Suitable materials for the insulative sheath or other member 594, 694, 794, 894 can include medical grade polymers, such as silicone and polyurethane, which can be engineered to create a desired degree of flexibility for bending during surgery. Suitable materials can also have a low coefficient of friction, such as PTFE, polyperfluoroalkoxy (PFA), fluorinated ethylene-propylene (FEP), polyethylenechlorotrifluoro-ehtylene (ECTFE), silicone rubber, polyurethane, and styrene-ethylene-butylene-styrene block polymer.

FIGS. 9-14 are enlarged schematic illustrations of distal end portions 962, 1062, 1162, 1262, 1362, 1462 of an example pacing guidewire's elongate body 950, 1050, 1150, 1250, 1350, 1450. The distal end portion of the elongate body can have a preformed shape 990, 1090, 1190, 1290, 1390, 1490, such as a pigtail shape (FIGS. 9-11), a J-shape (FIGS. 12 and 13), a V-shape (FIG. 14) or other non-linear shape, prior to surgery to provide a relatively long, gentle bend that limits the risk of damage to delicate tissue (e.g., vessel walls, aortic or mitral valves, or ventricular walls) during introduction and positioning of the guidewire within a patient or to provide a region to conform to anatomical shapes (e.g., the ventricular apex). A prearranged loading tool can be included with the guidewire for straightening and facilitating introduction of its distal end portion into a guide catheter. As will be appreciated, the introduction of an elongate resilient bend can minimize the likelihood of trauma to the patient by transmitting forces applied to cardiac tissues and structures by the guidewire along a dispersed, radial path rather than along a concentrated, longitudinal path via the guidewire's tip. The looping bend can also provide for a longer transition between the stiff support section of the guidewire and the softer atraumatic distal end portion. In an example, the distal end portion has relatively enhanced flexibility and low tip stiffness (e.g., 1 g, 2 g, 3 g, 4 g or 5 g) such that the preformed shape can instantly curve into its unbiased shape upon discharge from the guide catheter.

To form the preformed biased shape 990, 1090, 1190, 1290, 1390, 1490, a corewire, a surrounding conductor, or both, can be constructed of a superelastic material, such as a nickel-titanium alloy, and can be manufactured in the biased shape to thus bias the elongate body 950, 1050, 1150, 1250, 1350, 1450. The distal end portion of the corewire, the surrounding conductor, or both, can optionally be shaped during a thermal shape setting process. As part of the process, the distal end portion(s) can be inserted into a sleeve that is shaped into a desired configuration. Heat can then be applied to the distal end portion(s) through the sleeve for a period of time. Once cooled and removed from the sleeve, the corewire, the surrounding conductor, or both, can be permanently imparted with the desired shape. Accordingly, although the elongate body 950, 1050, 1150, 1250, 1350, 1450 can be reconfigured upon applying a suitable force thereon (e.g., straightened during insertion through a guide catheter), the thermal treatment of the corewire, the surrounding conductor, or both, can cause the distal end portion of the elongate body to resiliently return to its preformed configuration in the absence of forces.

Figure 9:
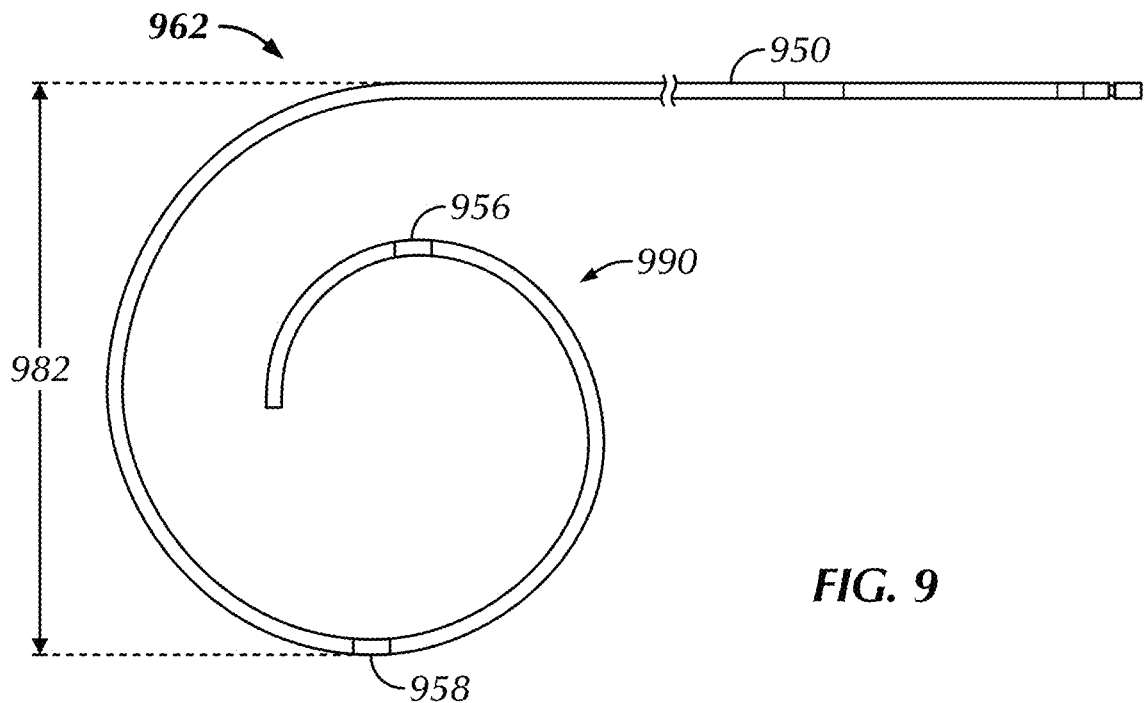
Figure 10:
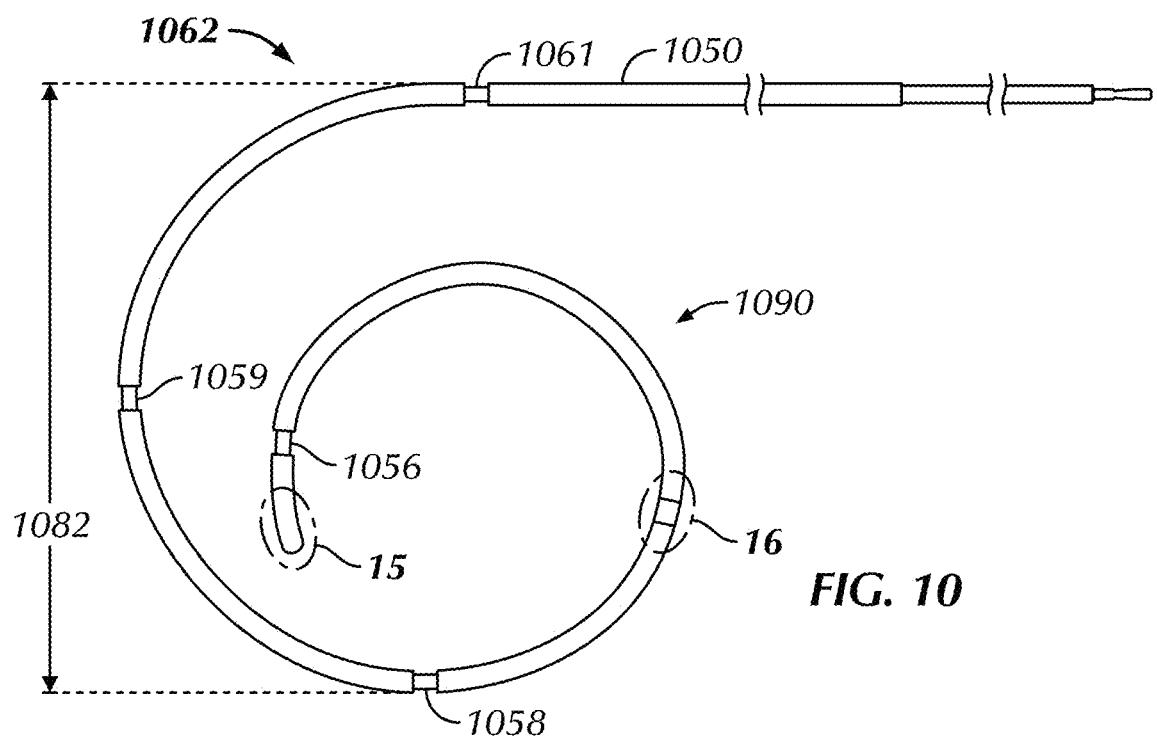

As shown in the examples of FIGS. 9-14, first and second electrodes 956, 958, 1056, 1058, 1156, 1158, 1256, 1258, 1356, 1358, 1456, 1458 can be spaced apart along, and supported by, the preformed shape 990, 1090, 1190, 1290, 1390, 1490. Optionally, as shown in the example of FIG. 10, third and fourth electrodes 1059, 1061 can also be spaced along the preformed shape 1090 and can have the same polarity as the second electrode 1058 (via connection to the same conductor). The addition of the third and fourth electrodes 1059, 1061 can increase the likelihood of electrode contact with heart wall tissue.

Figure 11:
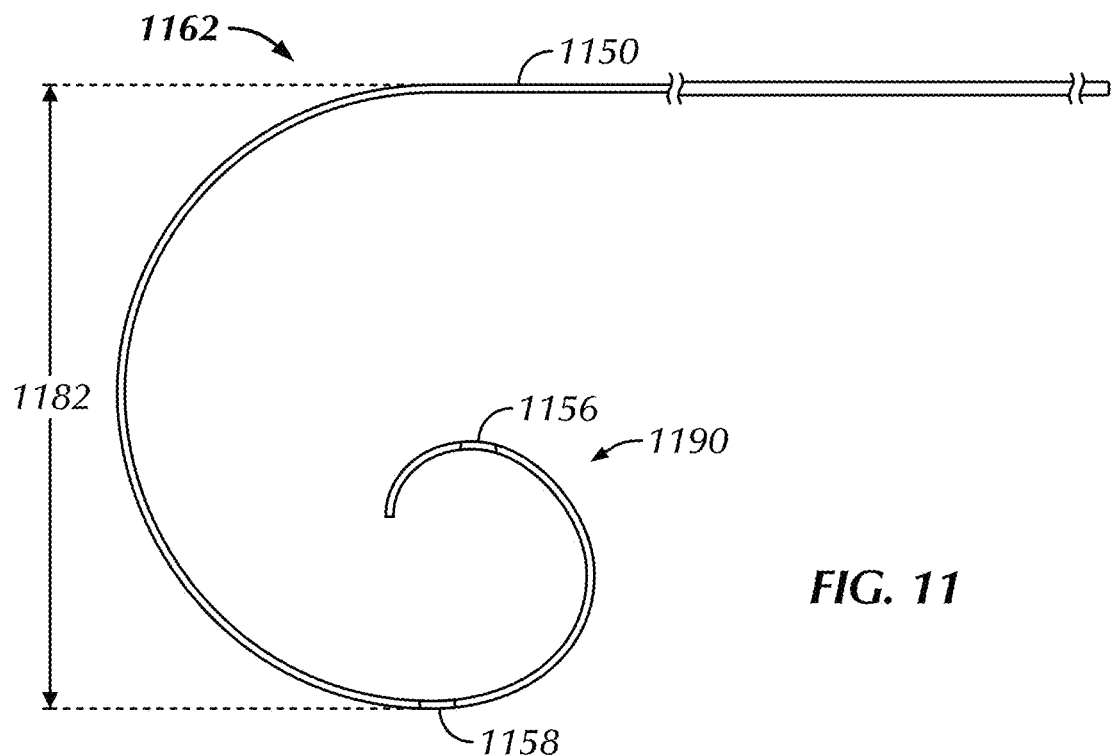
Figure 12:
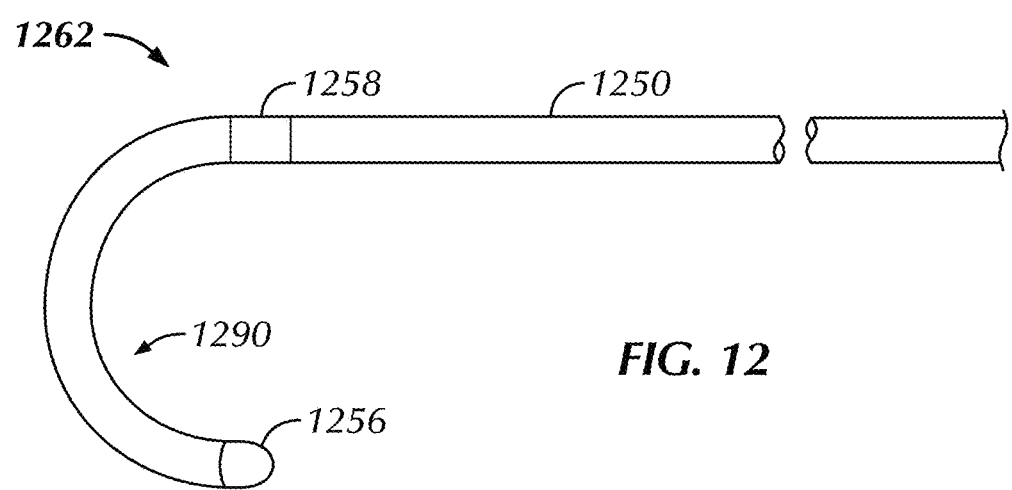

The pigtail shape 990, 1090, 1190 of FIGS. 9-11 can have a side height 982, 1082, 1182 of between about 20 mm-40 mm, can turn through more than 270 degrees, more than 360 degrees or more than 540 degrees, and can be composed of a corewire and one or more helical coils, for example. The present inventors have found that multiple nested loops (e.g., a first loop within a second loop) make it even less likely that the distal end portion of the guidewire can cause trauma to bodily tissue during its positioning. The corewire can be made from an electrically-conductive material and, alone or in combination with a first helical coil or other structure, can form one of the guidewire's elongate conductors. For example, as shown in FIG. 15, a corewire 1580 can be electrically coupled to a first helical coil or first helical coil portion 1584a to form an elongate conductor. A second helical coil or second helical coil portion can surround a portion of the corewire and, alone or in combination with another structure(s) (e.g., hypotube and/or braid), can form the second of the guidewire's conductors. As shown in FIG. 16, first and second helical coils or helical coil portions 1684a, 1684b can be longitudinally separated by a coil insulator 1679 positioned between a guidewire's two electrodes having opposite polarities.

Each helical coil or helical coil portion can include one or more filars and can be constructed from an appropriate formable material, such as but not limited to stainless steel, that is surrounded by insulation optionally applied with a lubricious coating on its exterior surface to facilitate advancement and retraction of the guidewire through the guide catheter. The use of a stainless steel material to form the helical coils can render them radiolucent. Accordingly, a portion of the helical coils can be applied with a radiopaque surface treatment (e.g., a platinum, palladium, gold, tantalum, or tungsten-based treatment) to render them highly visible under fluoroscopy.

The pigtail shape 990, 1090, 1190 of FIGS. 9-11 can optionally have a gradual reduction in cross-sectional diameter toward its distal end, and the radius of curvature of the pigtail shape can also decrease toward the distal end. This can provide a resulting pacing guidewire that has adequate stiffness to be inserted into a heart and provides support for items delivered OTW (e.g., aortic valve implantation systems), while also having flexibly and resilience so that it can maintain at least one electrode in contact with a ventricular wall in the presence of factors such as the beating of the heart and patient movement, both of which can interrupt engagement between an electrode and the ventricular wall.

The preformed shape of the distal end portion of the guidewire's elongate body need not be constructed as a single plane structure. Rather, since the space within the left ventricle is multi-planar, the preformed shape 1390 of the distal end portion 1362 can be constructed as a multi-planar structure, as shown in FIG. 13. The distal end portion 1362 can be non-coplanar relative to adjacent distal end portions or relative to the proximal or intermediate portions of the elongate body. In an example, the distal end portion 1362 is disposed at an angle 1392 relative to a plane containing the central axis of an intermediate portion 1364 of the elongate body, where the angle is between about 2 degrees and about 30 degrees.

FIGS. 17-19 are enlarged schematic illustrations of example electrode configurations designed to contact and stimulate heart tissue. A distal end portion 1762, 1862, 1962 of an elongate body 1750, 1850, 1950 can be provided with at least first and second electrodes 1756, 1758, 1856, 1858, 1956, 1958 spaced apart by an insulative sheath or other member 1794, 1894, 1994. The electrodes 1756, 1758, 1856, 1858, 1956, 1958 can be electrically connected through or along the elongate body 1750, 1850, 1950 by first and second conductors to the proximal end portion of the elongate body. In an example, the first electrode 1756, 1856, 1956 can be provided at or near the distal end portion of the guidewire, and the second electrode 1758, 1858, 1958 can be spaced rearward (or more proximal) from the first electrode. Each electrode can beneficially be formed of platinum, carbon, iridium or titanium, for example, and its surface can optionally be treated using chemical, mechanical, or electrical and mechanical methods to improve resistance to polarization or decrease the stimulation threshold. One or both electrodes can be radiopaque to assist in fluoroscopic location of the measurement site.

It is within the contemplation of the present pacing guidewires that there be no separate electrode structure and an exposed surface of a conductor in which the insulative sheath has been removed can be an electrode. The insulative sheath can be removed about the entire circumference of the conductor, forming a ring-shaped electrode surface, or only a portion of the insulative sheath can be removed circumferentially about the conductor, forming a semi-ring shaped electrode surface. Exposing a length of a conductor to allow it to be the electrode has the advantage of eliminating a connection between a separate electrode structure and the conductor.

In the example of FIG. 17, first and second conductors 1752, 1754 in the form of helical coils 1784a, 1784b of differing diameters and insulated from one another prior to winding are shown. The first conductor 1752 can extend more distal than the second conductor 1754 and can electrically connect to a first electrode 1756. The first electrode 1756 can comprise a cup-shaped element defining the leading tip of the guidewire. A portion(s) of the insulation covering the second conductor 1754 can be removed to form second, more proximal electrode(s) 1758. In embodiments where multiple electrode contacts are connected to the same conductor, the electrode with the best tissue contact, as determined by a pacing system analyzer (PSA), can serve as the stimulating electrode. This configuration can allow for a decrease in stimulation threshold.

Alternatively, as shown in the example of FIG. 18, a second, more proximal electrode 1858 can comprise a ring electrode spaced from a first, more distal electrode 1856. The electrical connection between a second conductor 1854 and the ring electrode can be by means of a crimp ring. The crimp ring can have a length approximately one-half the axial length of the ring electrode. In effecting the connection of the second conductor 1854 to the second electrode 1858, the distal end portion of the conductor can be brought out from the guidewire at a point adjacent the distal end of the crimp ring. The conductor 1854 can be folded back toward the proximal end portion of the guidewire. The electrode 1858 can then be slipped over the guidewire and the crimp ring can clamp the end of the conductor 1854 therebetween. Upon installation of the electrode 1858, the assembly can be dipped in a suitable adhesive material to fill the bore from which the conductor 1854 may be removed in bringing its distal end portion outwardly from the guidewire. The electrode 1858 can be formed with connector elements on its inner surface to receive the distal end portion of the conductor in a variety of other ways as well.

In the example of FIG. 19, an outer surface of each of first and second electrodes 1956, 1958 can be raised beyond an outer surface of the elongate body 1950. Electrodes designed in this fashion can increase the chances of achieving intimate tissue-electrode contact resulting in lower pacing thresholds.

Figure 20:
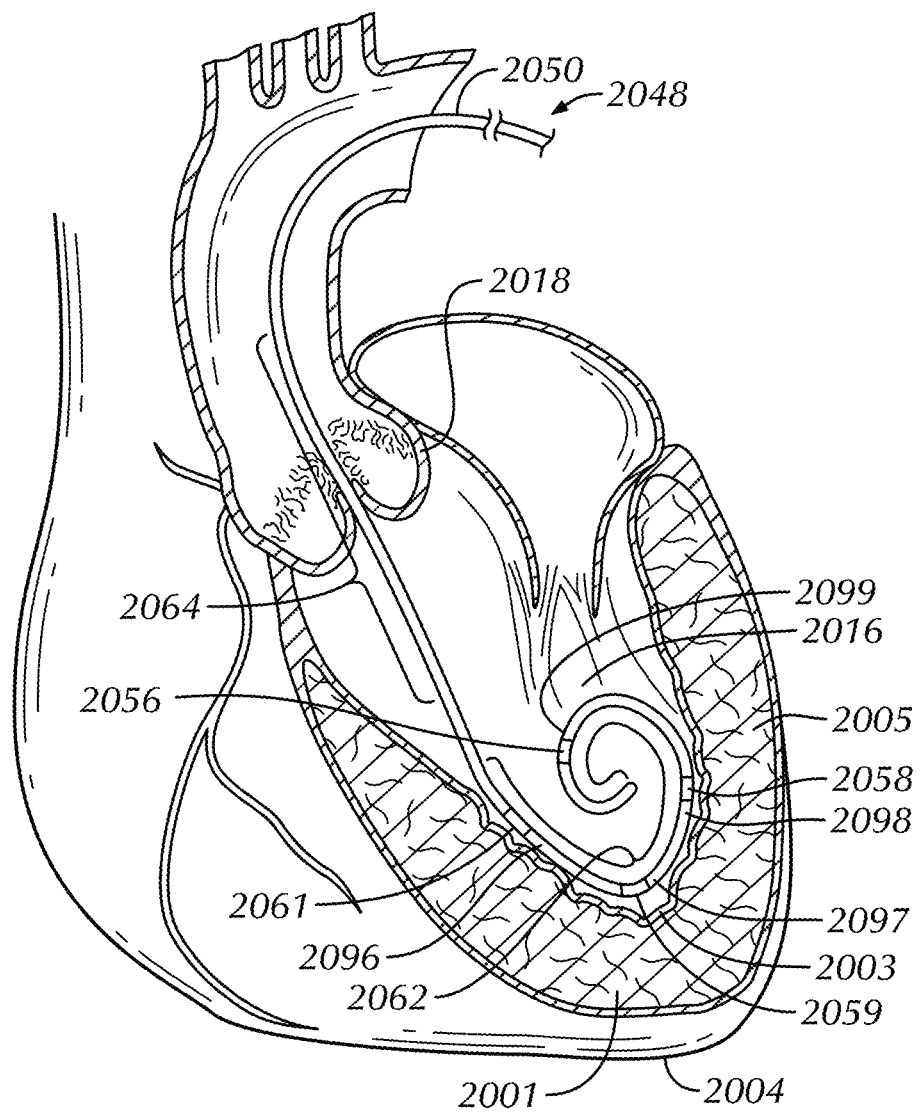
FIG. 20 is a schematic illustration of an example pacing guidewire positioned within a left ventricle of a heart.

Interplay of Example Pacing Guidewire and Heart:

FIG. 20 is a schematic illustration of an example pacing guidewire 2048 positioned within a left ventricle 2016 of a heart 2004. In this position, the guidewire 2048 can provide good support for the OTW delivery of elongate aortic valve treatment devices and can provide electrical stimuli to the left ventricle 2016 to induce and maintain cardiac ventricular tachycardia during medical procedures such as TAVI, TAVR and BV.

The guidewire 2048 can include an elongate body 2050 having an intermediate portion 2064 positioned within an aortic valve 2018 and a distal end portion 2062 extending into the left ventricle 2016. The distal end portion 2062 can conceptually be separated into a first region 2096 configured to contact a ventricular wall 2001 on a first side of a ventricular apex 2003, a second region 2097 configured to span across the apex 2003, a third region 2098 configured to contact a ventricular wall 2005 on a second side of the apex 2003, and/or a fourth region 2099 configured to curve away from the ventricular wall 2005 on the second side of the apex 2003.

Electrode means conductively connected to the distal end portion 2062 of the elongate body 2050 can provide low resistant and low impedance electrical interfaces with bodily fluid and excitable tissue in contact with, or in the vicinity of, the electrode means. In the example shown, a first electrode 2056 is disposed on the fourth region 2099, a second electrode 2058 is disposed on the third region 2098, a third electrode 2059 is disposed on the second region 2097, and a fourth electrode 2061 is disposed on the first region 2096. The second, third and fourth electrodes 2058, 2059, 2061 can have an opposite polarity as the first electrode 2056, and collectively, these electrodes can serve as the positive and negative poles during pacing and can be maintained in good electrical contact with the walls of the left ventricle 2016 directly or indirectly via blood or other fluid. By way of example, the first electrode 2056 can serve as the anode, and the second, third and fourth electrodes 2058, 2059, 2061 can serve as the cathode. The present inventors have found that advantageous (low) capture and pacing thresholds can be achieved when at least the cathode is in direct or near direct contact with heart tissue (e.g., wall tissue of the left ventricle).

Temporary Pacing Laboratory Tests and Animal Trials:

The energy transmission to the heart provided by two electrodes positioned within a left ventricle was investigated not only in laboratory tests, but also in practical animal trials.

First Animal Trial:

Temporary pacing of a pig's heart using two electrodes positioned in the left ventricle was successfully performed with a fraction of the energy required to capture and pace the heart relative to using conventional temporary pacing, which, as shown in FIG. 1, involves a femoral or jugular venous puncture to place a unipolar pacing lead (first electrode) in a right ventricle and a second electrode on a patient's skin.

The present inventors also discovered that substantially less energy is required to pace a pig's heart using two electrodes positioned in the left ventricle relative to using a first electrode positioned at the skin's surface or in the aorta and a second electrode positioned in the left ventricle, as the following findings show.

| Negative Pole | Positive Pole | Capture Threshold |
|---|---|---|
| Guidewire having a fully exposed pigtail at its distal end portion positioned in left ventricle | Electrode pad on back | 7 mA |
| Guidewire having a fully exposed pigtail at its distal end portion positioned in left ventricle | Electrode clamp attached to skin near femoral access point | 5.5 mA |
| Guidewire having a fully exposed pigtail at its distal end portion positioned in left ventricle | Electrode needle in chest | 3.5 mA |
| Guidewire having a fully exposed pigtail at its distal end portion positioned in aorta | Guidewire having a partially exposed straight distal end portion positioned at apex in left ventricle | 4.0 mA |
| Guidewire having a partially exposed pigtail at its distal end portion positioned in aorta | Guidewire having a partially exposed straight distal end portion positioned at apex in left ventricle | 3.5 mA |
| Guidewire having a partially exposed straight distal end portion positioned in left ventricle with no ventricular wall contact | Pacing lead having a distal electrode positioned at apex in left ventricle | 0.3 mA |

Second Animal Trial:

Three embodiments of the present bipolar pacing guidewire were tested for capture threshold in two different locations—the apex and mid-left ventricle—within a pig's heart. Rapid pacing ability and functionality during inflation of a 20 mm Edwards-Sapien™ 3 heart valve delivery system (Edwards Lifesciences, Irvine, CA) were also tested. The primary objective was to demonstrate consistently acceptable rapid pacing capture thresholds and persistent pacing induced hypotension under a series of unique conditions and positions. Capture thresholds were evaluated with pacing guidewires positioned in the left ventricular apex and mid-cavity at a rate of 130 bpm using both positive and negative polarity at the distal node. Rapid pacing ability was confirmed at 180 bpm with balloon inflation.

Figure 21:
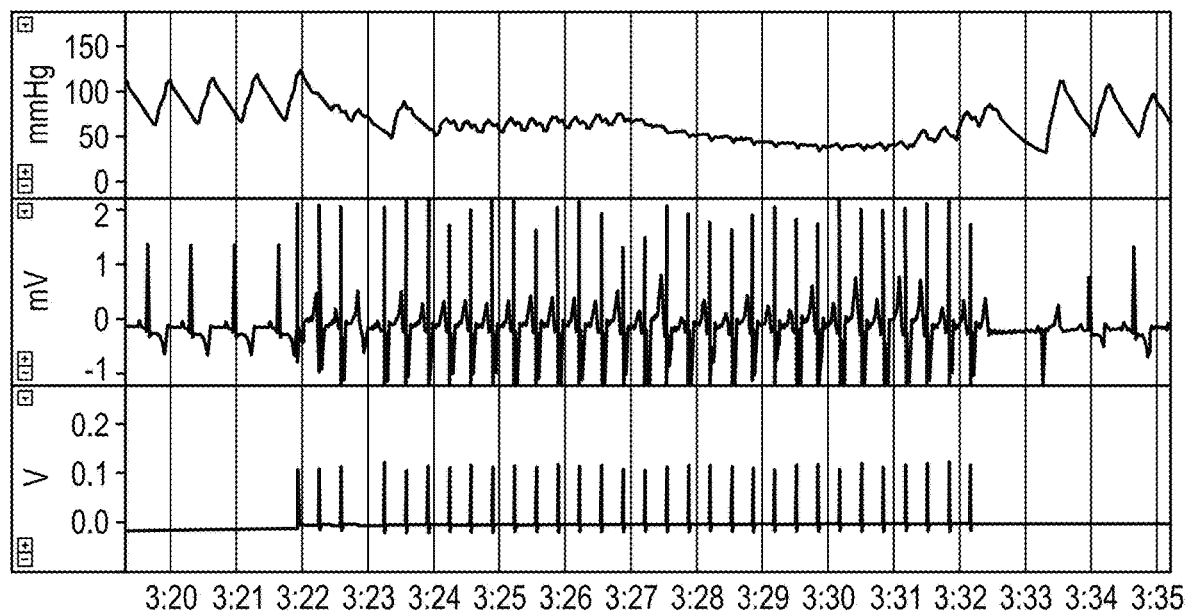
FIG. 21 is a graph illustrating invasive blood pressure (top), an intracardiac electrocardiogram (middle), and pacing spikes (bottom) during rapid left ventricular pacing of a pig's heart using an example pacing guidewire.
Figure 22:
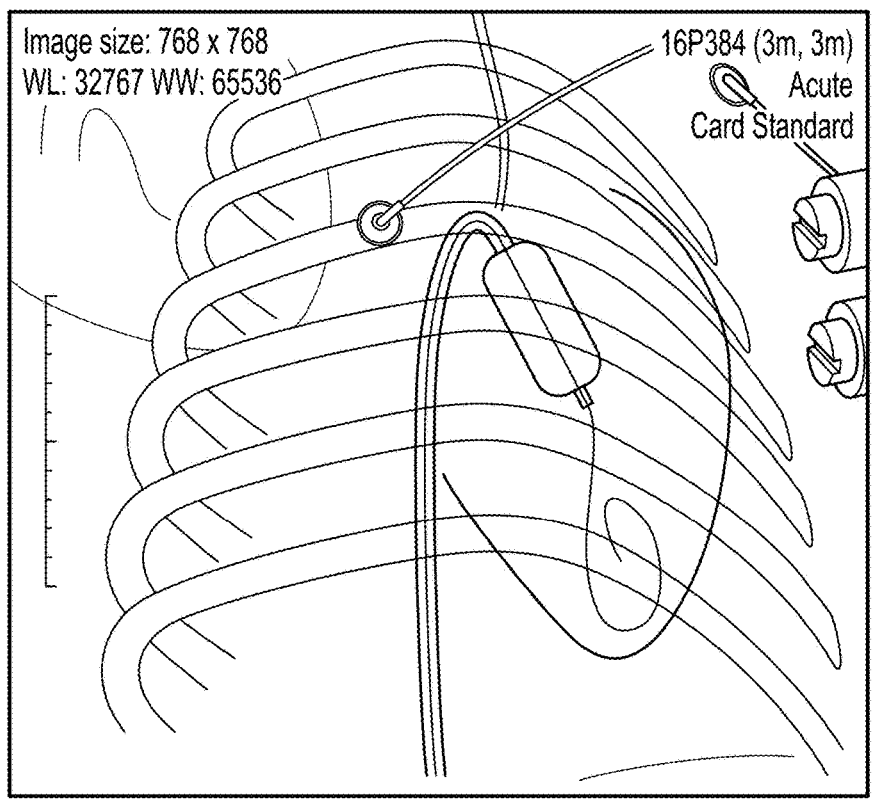
FIG. 22 is a diagnostic image illustrating an example pacing guidewire supporting the delivery of a heart valve system.

Using the bipolar pacing guidewires, capture thresholds were 1.2+/−0.36 mA when the wire was positioned at the left ventricular apex and 1.75+/−0.25 mA when the wire was positioned in the left ventricle mid-cavity, out of contact with the apex. Rapid pacing at 180 bpm was then successfully achieved with all pacing guidewires at 2× capture threshold (FIG. 21). The Edwards-Sapien™ 3 heart valve delivery system was subsequently introduced and re-confirmed consistent rapid pacing ability at 2× capture threshold during delivery system inflation (FIG. 22).

As a control, unipolar left ventricular pacing was tested in a second pig model using an Amplatz Super Stiff guidewire (Boston Scientific Corporation, Boston, MA) and ground using a 22 gauge needle in subcutaneous tissue. The guidewire was insulated with a 5 French AR1 diagnostic catheter. Capture threshold testing was repeated in the mid-cavity and left ventricular apical positions and rapid pacing at 180 bpm.

In the control arm, capture thresholds were 6.0 mA and 5.0 mA with the Amplatz Super Stiff guidewire in the mid-cavity and left ventricular apical positions, respectively. Rapid pacing at 180 bpm was also confirmed at 2× capture threshold in both positions.

Figure 23:
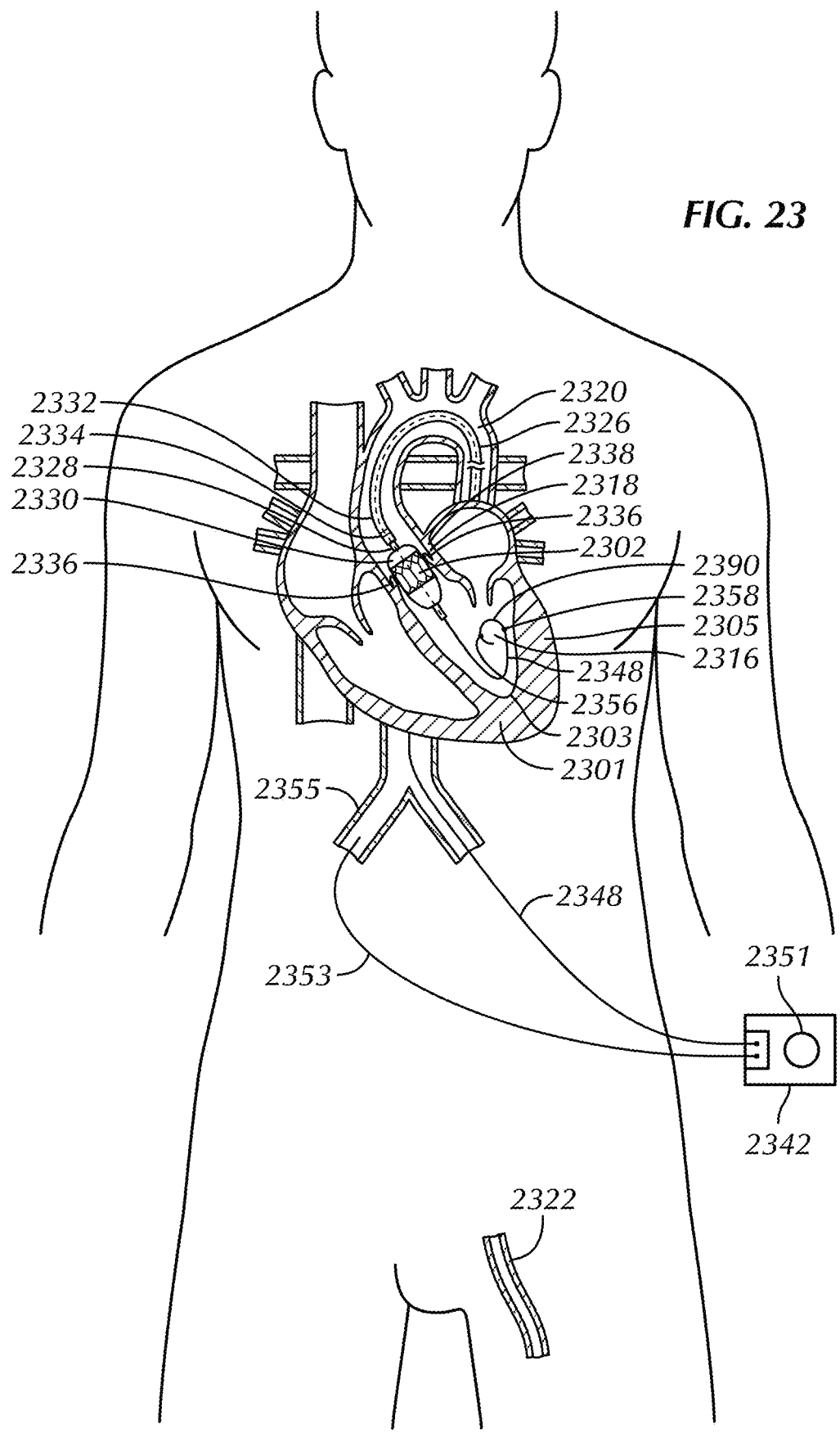
FIG. 23 is a schematic illustration of the implantation of a prosthetic aortic heart valve using an example pacing guidewire and an external pulse generator.

Transfemoral TAVI, TAVR and BV Procedures Using Example Pacing Guidewire:

FIG. 23 is a schematic illustration of a prosthetic aortic heart 2302 valve being implanted using an example pacing guidewire 2348, and an optional closed loop external pulse generator 2342. The guidewire 2348 can be designed as both an OTW delivery wire (e.g., to reliably guide aortic valve delivery systems and implants to a desired site) and a bipolar pacing means, thereby obviating the need for a dedicated right ventricular pacing system, which has been conventionally used and is illustrated in FIG. 1. The guidewire 2348 can be a one-time use disposable device and a proximal connector body can be designed to be compatible with a reusable external pulse generator 2342.

As part of the valve implantation procedure, the guidewire 2348 can be inserted through a guide catheter that extends from a femoral artery 2322, through an ascending aorta 2320, and within the aortic valve 2318 of a patient. The guidewire 2348 can be advanced through the guide catheter until its distal end portion projects into a left ventricle 2316 and assumes a preformed bias (e.g., pigtail) shape 2390. As shown, the guidewire 2348 can travel along an arcuate path made up of a ventricular wall 2301 on a first side of a ventricular apex 2303, the ventricular apex 2303, and a ventricular wall 2305 on a second side of the ventricular apex 2303 as it is advanced into the left ventricle. In one example, when the guidewire 2348 is fully advanced into the left ventricle 2316, a first electrode 2356 can be positioned a spaced distance from the ventricular wall 2305 on the second side of the ventricular apex, a second electrode 2358 can be positioned against this ventricular wall 2305, and the guide catheter can be removed from the patient.

Positioned as such within the left ventricle, the guidewire 2348 can be used to transmit electrical stimuli from the external pulse generator 2342 to the first and second electrodes 2356, 2358 to induce and maintain cardiac ventricular tachycardia, thereby resulting in reduced cardiac output to allow balloon deployment in the aortic annulus without embolization from cardiac flow. The electrical stimuli can be sufficiently slow to capture the ventricular myocardium in a 1:1 manner, while being sufficiently fast to lower the systolic blood pressure to less than about 70 millimeters of mercury (mmHg) and the pulse pressure to less than about 20 mmHg. In some examples, the transmitted electrical stimuli can result in a current flow of 3.0 mA or less between the first and second electrodes 2356, 2358 (during full pacing) or 1.5 mA or less between the first and second electrodes 2356, 2358 (during initial capture) and ventricular rates of 120-220 beats per minute (bpm).

Medical procedures utilizing the pacing guidewire 2348 as a delivery and support means can then be performed on the heart while it is maintained in a state of ventricular tachycardia. For example, an introducer sheath 2326 can be inserted over the guidewire 2348 and into the ascending aorta 2320, with a balloon catheter 2328, having a dilatation balloon 2330 on its distal end portion, passed over the guidewire 2348 and through the sheath 2326. A physician can locate a distal tip 2332 of the introducer sheath 2326 using a radiopaque marker(s) 2334, for example, and the dilatation balloon can be expanded radially outward into contact with native aortic valve leaflets 2336 as part of a BV procedure. With information concerning the size of the particular aortic valve 2318, the balloon 2330 can be chosen so that it expands outward and nominally compresses the aortic valve leaflets 2336 against the surrounding aortic walls 2338.

The physician or operating room staff can then crimp the expandable prosthetic aortic heart valve 2302 over the dilatation balloon 2330. With the prosthetic heart valve 2302 crimped over the balloon 2330, the physician can once again advance the balloon catheter 2328 over the guidewire 2348 and through the introducer sheath 2326 until the prosthetic heart valve 2302 is located at the aortic annulus and between the native aortic leaflets 2336. When the physician is satisfied with the positioning and rotational orientation of the prosthetic heart valve 2302, the balloon 2330 can be expanded into good contact with the aortic annulus. Once the valve is properly implanted, the physician can deflate the balloon 2330 and withdraw the balloon catheter 2328 over the guidewire 2348. The introducer sheath 2326 can then be withdrawn simultaneously with, or followed by, the guidewire 2348.

The external pulse generator 2342 can optionally contain electronics and software necessary to detect certain electrophysiological responses to the electrical stimuli and then adjust the transmitted stimuli in a closed loop manner (i.e., control the functioning of a heart in accordance with information obtained about its mechanical state). The pulse generator 2342 may be designed specifically for temporary use as part of a system to perform TAVI, TAVR or BV in which the goal is to drop blood pressure and cardiac output below a prespecified level to allow for safe balloon deployment. When cardiac output is below the prespecified level for safe balloon deployment, an indicator light 2351 on the pulse generator 2342 can change from red to green.

The electrophysiological responses can, in some examples, be detected from an intra-arterial pressure monitor 2353 positioned in a central artery 2355 using an indwelling catheter that is an existing component of the medical procedure. Monitored pressure signals, such as systolic blood pressure or pulse pressure, can be processed using an algorithm and an electrical stimuli (pacing) rate can designed to achieve 1:1 ventricular capture in most patients, such as about 120 bpm to 220 bpm, can be calculated. If the pacing rate at any point leads to less than 1:1 capture of the ventricle (as monitored, for example, by the relationship between pacing frequency and systolic pressure rise), the pulse generator 2342 can decrease pacing frequency in order to capture the ventricle in a 1:1 fashion, then re-initiate the algorithm to increase pacing rate in order to meet the hemodynamic goals as stated above (systolic blood pressure less than about 70 mmHg and pulse pressure less than about 20 mmHg).

Closing Notes and Examples

TAVI, TAVR, BV and TMVR procedures are occurring with increasing frequency throughout the world. Further commercialization and development of new and alternative devices to facilitate such procedures are only going to encourage this trend.

The present pacing guidewires and methods can minimize procedural times, obviate potential complications, and optimize outcomes in TAVI, TAVR, BV and TMVR procedures. For example, the pacing guidewires can be configured to provide good support for the OTW delivery of elongate treatment devices with less chance of perforation or other damage of vessels, the native aortic or mitral valve, or cardiac tissues through which the guidewires are inserted. Pacing electrodes, by being part of each guidewire and insulated from one another, can minimize the steps and risks of the valve procedures by obviating the need for an additional venous puncture for insertion of a dedicated right ventricular temporary pacing lead and can be ready for capture tests or pacing without a delivery system in place.

Laboratory and animal trials have proven the safety and efficacy of cardiac pacing using electrodes associated with the pacing guidewires as an alternative to the traditional approach of separate dedicated temporary pacing leads. The animal trials, for example, suggest capture thresholds on par with traditional temporary right ventricular pacing leads (but without the associated risks) and significantly lower capture thresholds than those seen with standard guidewires acting as a unipolar system in the left ventricle. Unlike standard guidewires, the present pacing guidewires do not require insulation in the form of an over-the-wire delivery device to function, and therefore threshold testing can be carried out immediately after placement. Furthermore, the mechanical properties of these pacing guidewires, including a pre-shaped tip, demonstrated no preliminary safety concerns during delivery of a balloon-expandable valve delivery system from a femoral artery to a native aortic valve.

The above Detailed Description includes references to the accompanying drawings, which form a part of the Detailed Description. The Detailed Description should be read with reference to the drawings. The drawings show, by way of illustration, specific embodiments in which the present pacing guidewires and methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a method for transmitting electrical stimuli to a patient's heart and for guiding and supporting the delivery of elongate treatment devices within the heart can comprise advancing a distal end portion of a bipolar pacing guidewire into the left ventricle such that first and second electrodes are positioned against or spaced from a ventricular wall. Electrical stimuli can be transmitted through the guidewire to the first and second electrodes to induce and maintain cardiac ventricular tachycardia. While the heart is in a state of ventricular tachycardia, a medical procedure can be performed.

In Example 2, the method of Example 1 can optionally be configured such that advancing the distal end portion of the bipolar pacing guidewire into the left ventricle includes advancing a resiliently deformable, pre-formed curved shape into the left ventricle.

In Example 3, the method of Example 2 can optionally be configured such that the pre-formed curved shape includes a pigtail-shaped region that turns through 540 degrees or more, and the first and second electrodes are spaced apart on the turns.

In Example 4, the method of any one or any combination of Examples 1-3 can optionally be configured such that positioning the first and second electrodes includes positioning the first electrode a spaced distance from the ventricular wall and positioning the second electrode against the ventricular wall.

In Example 5, the method of Example 4 can optionally be configured such that the first electrode is an anode and the second electrode is a cathode.

In Example 6, the method of any one or any combination of Examples 1-3 can optionally be configured such that positioning the first and second electrodes includes positioning the first electrode against a ventricular wall on a first side of a ventricular apex and positioning the second electrode against a ventricular wall on a second side of the ventricular apex.

In Example 7, the method of any one or any combination of Examples 1-6 can optionally be configured such that transmitting electrical stimuli through the guidewire to the first and second electrodes includes transmitting electrical stimuli through a first elongate conductor electrically connected to the first electrode and transmitting electrode stimuli through a second elongate conductor electrically connected to the second electrode.

In Example 8, the method of Example 7 can optionally be configured such that transmitting electrical stimuli through the first elongate conductor includes transmitting electrical stimuli through a corewire and a helical coil.

In Example 9, the method of any one of Examples 7 or 8 can optionally be configured such that transmitting electrical stimuli through the second elongate conductor includes transmitting electrical stimuli through a hypotube or a braid and a helical coil.

In Example 10, the method of any one or any combination of Examples 1-9 can optionally be configured such that transmitting electrical stimuli to the first and second electrodes includes generating a current flow of 4.0 mA or less between the electrodes.

In Example 11, the method of Example 10 can optionally be configured such that transmitting electrical stimuli to the first and second electrodes includes generating a current flow of 3.0 mA or less between the electrodes.

In Example 12, the method of any one or any combination of Examples 1-11 can optionally be configured such that inducing and maintaining cardiac ventricular tachycardia includes inducing ventricular rates of 120-220 bpm and lowering the patient's blood pressure.

In Example 13, the method of any one or any combination of Examples 1-12 can optionally be configured such that performing the medical procedure includes delivering a balloon catheter over the pacing guidewire until a dilatation balloon, at a distal end portion of the balloon catheter, is positioned within a native aortic valve, and then radially expanding the dilatation balloon into contact with a native heart valve annulus.

In Example 14, the method of any one or any combination of Examples 1-12 can optionally be configured such that performing the medical procedure includes delivering a balloon catheter over the pacing guidewire until a dilatation balloon, at a distal end portion of the balloon catheter, is positioned within a native aortic valve, and then radially expanding the dilatation balloon to urge a prosthetic heart valve into contact with the native aortic valve.

In Example 15, the method of any one or any combination of Examples 1-14 can optionally be configured such that performing the medical procedure includes delivering a balloon catheter over the pacing guidewire until a dilatation balloon, at a distal end portion of the balloon catheter, is positioned within a native mitral valve, and then radially expanding the dilatation balloon to urge a prosthetic heart valve into contact with the native mitral valve.

In Example 16, the method of any one or any combination of Examples 14 or 15 can optionally further comprise adjusting the electrical stimuli transmitted through the guidewire once the dilatation balloon is deflated.

In Example 17, the method of any one or any combination of Examples 1-16 can optionally further comprise sensing an electrophysiological response to the electrical stimuli transmitted through the guidewire, and adjusting the transmitted electrical stimuli through the guidewire based on the electrophysiological response.

In Example 18, the method of Example 17 can optionally be configured such that sensing the electrophysiological response includes sensing if less than a 1:1 capture of the left ventricle exists.

In Example 19, the method of Example 17 can optionally be configured such that sensing the electrophysiological response includes sensing the patient's systolic blood pressure or pulse pressure.

In Example 20, the method of Example 19 can optionally be configured such that adjusting the transmitted electrical stimuli includes increasing the electrical stimuli transmitted through the guidewire if the patient's systolic blood pressure is less than 70 mmHg or the pulse pressure is less than 20 mmHg.

In Example 21, the method of any one or any combination of Examples 1-20 can optionally further comprise removably coupling a connector body to a proximal end portion of the bipolar pacing guidewire, including electrically coupling first and second terminals of the connector body to first and second elongate conductors respectively associated with the first and second electrodes.

In Example 22, the method of Example 21 can optionally be configured such that removably coupling the connector body to the proximal end portion of the bipolar pacing guidewire includes preventing shorting between the first and second elongate conductors.

In Example 23, the method of any one or any combination of Examples 1-22 can optionally be configured such that all elements or options recited are available to use or select from.

The scope of the present methods should be determined with reference to the appended claims, along with the full scope of equivalents to which such claims are entitled. In the appended claims, the terms "including" and "in which" are used as the plain-English equivalents of the respective terms "comprising" and "wherein." Also in the following claims, the terms "including" and "comprising" are open-ended; that is, a method that includes features or components in addition to those listed after such a term in a claim are still deemed to fall within the scope of that claim. Moreover, the terms "first," "second," "third," etc. in the following claims are used merely as labels, and such terms not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A pacing guidewire system for delivering electrical stimulation to a heart of a patient, the pacing guidewire system comprising:
a guidewire comprising an elongate body extending from a proximal end portion to a distal end portion, the elongate body having a first elongate conductor extending from the proximal end portion of the elongate body to at least one first electrode located along the distal end portion of the elongate body, and a second elongate conductor extending from the proximal end portion of the elongate body to at least one second electrode located along the distal end portion of the elongate body; and
a connector member configured to be removably coupled to the proximal end portion of the elongate body, the connector member comprising a set of separate electrical conductors extending between a guidewire connection portion and a pulse generator connection portion of the connector member, the connector member configured to provide a set of electrical connections between the first and second elongate conductors and an electrical pulse generator.

2. The pacing guidewire system of claim 1, wherein the pulse generator connection portion of the connector member comprises a cathode connection and an anode connection.

3. The pacing guidewire system of claim 1, wherein the pulse generator connection portion of the connector member is configured to make electrical connections with the electrical pulse generator using alligator clips.

4. The pacing guidewire system of claim 1, wherein each conductor of the set of separate electrical conductors included in the connector member is configured to carry an electrical current of up to 4.0 milliamperes.

5. The pacing guidewire system of claim 1, wherein the guidewire connection portion of the connector member includes an entrance seal member configured to electrically isolate the first elongate conductor and the second elongate conductor from one or more fluids present in a treatment area of a patient.

6. The pacing guidewire system of claim 1, wherein the first elongate conductor is at least partially formed as a corewire, and wherein the second elongate conductor is at least partially formed as a braid or as a hypotube.

7. The pacing guidewire system of claim 1, wherein each of the first elongate conductor and the second elongate conductor includes a separate dedicated terminal contact at the proximal end portion of the elongate body, each separate dedicated terminal contact is configured to form an electrical connection with a respective terminal of the guidewire connection portion of the connector member.

8. The pacing guidewire system of claim 1, wherein the pulse generator connection portion of the connector member is color coded for identification of a polarity of the first elongate conductor and a polarity of the second elongate conductor.

9. The pacing guidewire system of claim 1, wherein the guidewire connection portion is configured to be slid on and off the proximal end portion of the elongate body.

10. The pacing guidewire system of claim 1, wherein the set of separate electrical conductors included in the guidewire connection portion of the connector member is positioned within a common entrance seal member, and wherein the set of separate electrical conductors extends away from the guidewire connection portion of the connector member as separated electrical conductors with each one of the separated electrical conductors ending in a terminal forming the pulse generator connection portion of the connector member.

11. A connector member comprising:
a guidewire connection portion configured to removably couple to a proximal end portion of a bipolar pacing guidewire;
a pulse generator connection portion configured to couple to an electrical pulse generator; and
a first electrical conductor and a second electrical conductor, the first electrical conductor and the second electrical conductor extending from the guidewire connection portion to the pulse generator connection portion, wherein electrical stimulation from the electrical pulse generator is provided to the bipolar pacing guidewire through the first electrical conductor and the second electrical conductor.

12. The connector member of claim 11, wherein the guidewire connection portion is configured to be slid on and off the proximal end portion of the bipolar pacing guidewire.

13. The connector member of claim 11, wherein the pulse generator connection portion includes a set of markings to indicate a first polarity for the first electrical conductor and a second polarity for the second electrical conductor.

14. The connector member of claim 13, wherein the set of markings includes color-coded indicia.

15. The connector member of claim 11, wherein the guidewire connection portion includes an entrance seal member configured to electrically isolate the first electrical conductor and the second electrical conductor from one or more fluids present in a treatment area of a patient.

16. The connector member of claim 11, wherein the guidewire connector portion comprises a housing including a first guidewire connection terminal coupled to the first electrical conductor and a second guidewire connection terminal coupled to the second electrical conductor.

17. The connector member of claim 11, wherein the pulse generator connection portion includes a first pulse generator connection terminal coupled to the first electrical conductor and a second pulse generator connection terminal coupled to the second electrical conductor.

18. A method comprising:
advancing a guidewire that includes a first insulated conductor coupled to at least one first electrode and a second insulated conductor coupled to at least one second electrode into a chamber of a patient's heart;
coupling a proximal end portion of the guidewire to a first portion of a connector member;
coupling a second portion of the connector member to an electrical pulse generator so that the electrical pulse generator is electrically coupled to the first insulated conductor and to the second insulated conductor;
delivering electrical stimulation provided by the electrical pulse generator through the connector member to the at least one first electrode coupled to the first insulated conductor and to the at least one second electrode coupled to the second insulated conductor to induce and maintain tachycardia in the patient's heart; and
delivering a treatment device over the guidewire to the patient's heart while the patient's heart is maintained in a state of tachycardia.

19. The method of claim 18, wherein delivering the treatment device includes performing a valve treatment procedure on the patient's heart.

20. The method of claim 18, further comprising removing the connector member from the proximal end portion of the guidewire prior to advancing or retracting a catheter over the proximal end portion of the guidewire.

* * * * *